United States Patent
Low et al.

(10) Patent No.: US 10,406,238 B2
(45) Date of Patent: Sep. 10, 2019

(54) LIGAND IONOPHORE CONJUGATES

(71) Applicant: PURDUE RESEARCH FOUNDATION, West Lafayette, IN (US)

(72) Inventors: Philip Stewart Low, West Lafayette, IN (US); Venkatesh Chelvam, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/572,985

(22) PCT Filed: May 11, 2016

(86) PCT No.: PCT/US2016/031738
§ 371 (c)(1),
(2) Date: Nov. 9, 2017

(87) PCT Pub. No.: WO2016/183131
PCT Pub. Date: Nov. 17, 2016

(65) Prior Publication Data
US 2018/0154006 A1    Jun. 7, 2018

Related U.S. Application Data

(60) Provisional application No. 62/159,659, filed on May 11, 2015.

(51) Int. Cl.
| | | |
|---|---|---|
| A61K 31/35 | (2006.01) | |
| A61K 38/08 | (2019.01) | |
| A61K 45/06 | (2006.01) | |
| A61K 47/54 | (2017.01) | |
| A61K 47/55 | (2017.01) | |
| A61P 29/00 | (2006.01) | |
| A61P 35/00 | (2006.01) | |
| G01N 33/84 | (2006.01) | |
| G01N 33/533 | (2006.01) | |

(52) U.S. Cl.
CPC ............ *A61K 47/551* (2017.08); *A61K 31/35* (2013.01); *A61K 38/08* (2013.01); *A61K 45/06* (2013.01); *A61K 47/54* (2017.08); *A61P 29/00* (2018.01); *A61P 35/00* (2018.01); *G01N 33/84* (2013.01); *G01N 33/533* (2013.01)

(58) Field of Classification Search
None
See application file for complete search history.

(56) References Cited

U.S. PATENT DOCUMENTS

| | | | |
|---|---|---|---|
| 4,713,249 A | 12/1987 | Schroder | |
| 5,266,333 A | 11/1993 | Cady et al. | |
| 5,417,982 A | 5/1995 | Modi | |
| 2004/0242582 A1 | 12/2004 | Green et al. | |
| 2010/0324008 A1* | 12/2010 | Low .................. | A61K 49/0041 514/184 |
| 2011/0288152 A1 | 11/2011 | Low et al. | |
| 2014/0107316 A1* | 4/2014 | Vlahov ............. | A61K 47/48338 530/329 |
| 2014/0161827 A1* | 6/2014 | Santen ............. | A61K 47/48669 424/178.1 |

FOREIGN PATENT DOCUMENTS

| | | | |
|---|---|---|---|
| WO | WO 2003/097647 | 11/2003 | |
| WO | WO 2004/069159 | 8/2004 | |
| WO | WO 2006/012527 | 2/2006 | |
| WO | WO2007/006041 | 1/2007 | |
| WO | WO 2007/022493 | 2/2007 | |
| WO | WO 2007/022494 | 2/2007 | |
| WO | WO 2009/002993 | 12/2008 | |
| WO | WO 2009/026177 | 2/2009 | |
| WO | WO 2010/033733 | 3/2010 | |
| WO | WO 2010/045584 | 4/2010 | |
| WO | WO 2010/045598 | 4/2010 | |
| WO | WO 2011/106639 | 9/2011 | |
| WO | WO2012/112440 | 8/2012 | |
| WO | WO-2014012479 A1 * | 1/2014 | ............. A61K 39/39 |

OTHER PUBLICATIONS

Kularatne; J. Med. Chem. 2010, 53, 7767-7777. (Year: 2010).*
Skiera; Chem Biol Drug Des 2015, 86, 911-917. First published: Jan. 21, 2015. (Year: 2015).*
Huczyński; European Journal of Medicinal Chemistry 2015, 93, 33-41. Available online Jan. 27, 2015. (Year: 2015).*
PCT Search Report and Written Opinion for PCT/US2016/031738, completed Jul. 21, 2016.
Tsai, Esther H.R., et al., "In Vivo Mouse Fluorescence Imaging for Folate-Targeted Delivery and Release Kinetics," 2014, Biomedical Optics Express, vol. 5, No. 8, pp. 2662-2678.
Thomas, M. et al., "Ligand-targeted delivery of small interfering RNAs to malignant cells and tissues," Ann. NY Acad. Sci., 2009, 1175, 32-39.

* cited by examiner

*Primary Examiner* — Daniel R Carcanague
(74) *Attorney, Agent, or Firm* — Barnes & Thornburg LLP

(57) ABSTRACT

The invention described herein pertains to ligand-ionophore conjugates, that may also comprise a linked therapeutic agent or imaging agent, and pharmaceutical compositions containing the conjugates. Also described are methods of using the conjugates for increasing the endosomal accumulation and escape of a therapeutic agent, or an imaging agent.

18 Claims, 13 Drawing Sheets

LIGAND IONOPHORE CONJUGATES

CROSS REFERENCE TO RELATED APPLICATIONS

This application is a U.S. national stage application under 35 U.S.C. § 371(b) of International Application No. PCT/US2016/031738 filed May 11, 2016, which claims priority under 35 U.S.C. § 119(e) to U.S. Provisional Application No. 62/159,659, filed May 11, 2015, both of which are incorporated herein by reference in their entirety.

TECHNICAL FIELD

The invention described herein pertains to ligand ionophore conjugates, which may also comprise a linked therapeutic agent or a linked imaging agent, and pharmaceutical compositions containing the conjugates. Also described are methods of using the described conjugates for increasing the endosomal accumulation and escape of a therapeutic agent, or an imaging agent, that is internalized by endocytosis or an analogous process.

BACKGROUND AND SUMMARY OF THE INVENTION

Many diseases can be treated with a drug or a biologic agent (illustrative examples of biologic agents include nucleotides, e.g. siRNA, miRNA and the like; amino acids, including synthetic amino acids not occurring in nature; proteins, including enzymes, peptides, aptamers, antigens and the like; and antibodies, e.g. glycoproteins, immunoglobulins and the like). These drugs or biologics can be delivered into their target cells with targeting ligands, e.g. a folate receptor binding ligand, but their efficacy can be inhibited by an inability of the drug or biologic agent to be released from the endo some, for example, after folate-mediated endocytosis. Therefore discovery of new methods for "endosomal release" of trapped cargo into the cytoplasm would be useful for achieving increased efficacy of targeted drugs or biologics. It has been discovered that endosomal release can be facilitated by use of ligand ionophore conjugates to create osmotic pressure to rupture the endosomes containing the cargo using known ionophores that have low toxicity to healthy tissues. Without being bound by theory it is believed that nigericin, an ionophore and antiporter that couples efflux of $H^+$ ions to influx of $K^+$ ions, if delivered into cells, causes an osmotic imbalance inside endosomes leading to a swelling and/or disruption of the endosome and the release of the endosomal contents into cytoplasm. It will be appreciated that other $K^+$ ionophores like salinomycin that transport potassium ions can also be employed for endosomal release.

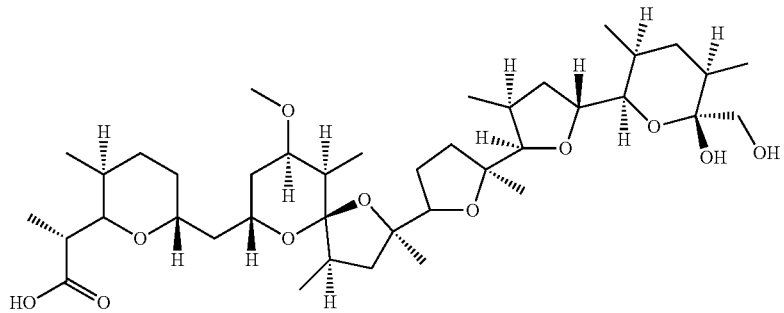

Nigericin, an ionophore

In order to induce swelling of an endosome, an osmotically active ion can enter the endosome and promote the accompanying osmotically driven influx of water. This influx of water should force the endosome to enlarge, ultimately leading to its rupture. However, if the influx of the osmotically active ion is accompanied by the efflux of another osmotically active ion, no net change in water flow will occur and the endosome will not expand. Thus, for endosome swelling to occur, an osmotically active ion (e.g., $Na^+$, $K^+$, $Li^+$, $Ca^{++}$, $Mg^{++}$) should enter the endosome in exchange for $H^+$, which is the only osmotically inactive cation in nature. Moreover, because the only osmotically active ion that will flow spontaneously down its concentration gradient into an endosome is $K^+$, an ionophore that is useful to lead to swelling of an endosome is an ionophore that can exchange $K^+$ ions for $H^+$ ions.

The $Na^+/H^+$ exchanger (antiporter) is a natural endosomal transporter whose function is to modify endosomal pH. It can work against a $K^+$ ionophore-induced endosomal swelling by moving sodium ions out of the endosome in exchange for $H^+$, leading to endosome shrinkage. Thus, the action of a $K^+$ ionophore might be reduced by a naturally occurring $Na^+/H^+$ exchanger (antiporter), but augmented by the simultaneous addition of an inhibitor of the $Na^+/H^+$ exchanger such as amiloride, or HOE 694, or the like.

Folate receptors are over expressed on the cell membrane of many human cancers like ovarian, lung, breast, endometrium, brain, kidney and colon cancer and in activated macrophages which are responsible for inflammatory diseases like rheumatoid arthritis, artherosclerosis, osteoarthritis, diabetes, psoriasis etc. Folic acid has high binding affinity ($K_d=10^{-10}M$) for folate receptors and can deliver releasable cargo to folate receptors in a selective manner avoiding off-site toxicity. Ligands bound to these receptors become part of the endosome that forms after the membrane invaginates into caveolae, internalizes and separates from the surface.

Prostate specific membrane antigen (PSMA) is a cell surface protein that is internalized in a process analogous to the endocytosis observed with cell surface receptors, such as folate receptors. It has been established that biologically active compounds that are conjugated via a linker to ligands capable of binding to PSMA may be useful in the imaging, diagnosis, and/or treatment of prostate cancer, and related diseases that involve pathogenic cell populations expressing or over-expressing PSMA. PSMA is over-expressed in malignant prostate tissues when compared to other organs in the human body such as kidney, proximal small intestine, and salivary glands. Although PSMA is expressed in brain, that expression is minimal, and most ligands of PSMA are polar and are not capable of penetrating the blood brain barrier. Unlike many other membrane-bound proteins, PSMA undergoes rapid internalization into the cell in a similar fashion to cell surface receptors like folate receptors. PSMA is internalized through clathrin-coated pits and subsequently can either recycle to the cell surface or be retained inside an endosome which progressively develops into a lysosome.

Even though a drug cargo delivered to a receptor capable of endocytosis, or an analogous process, is delivered selectively to the diseased cells, the path of delivered cargo to the cytoplasm or the nucleus can be blocked completely or partially by the invaginated plasma membrane called the 'endosome'. Higher molecular weight agents, such as peptides, siRNAs, antisense oligonucleotides, proteins, aptamers, oligosaccharides and polysaccharides cannot escape endosomes once they have been internalized via a ligand-targeted endocytosis pathway. Thus the trapped cargo stays in the endosome and finally decomposes to smaller fragments by the action of acids and enzymes present in the endosome before being released in inactive form. The conjugates of the invention increase both the endosomal accumulation and escape of a therapeutic agent, or an imaging agent in targeted cells.

Several embodiments of the invention are described in the following clauses:

1. A conjugate comprising:
   a ligand (B) targeted to a cell-surface receptor;
   a linker (L); and
   one or more ionophores (A) each of which couples efflux of protons ($H^+$ ions) to influx of potassium ions ($K^+$ ions);
   wherein (L) comprises at least one releasable linker; (B) is covalently linked to (L); and each (A) is covalently linked to (L).

2. The conjugate of clause 1 wherein (L) comprises at least one releasable linker.

3. The conjugate of clause 1 or 2 further comprising a therapeutic agent, and/or an imaging agent wherein the therapeutic agent or the imaging agent is covalently linked to (L).

4. The conjugate of any of clauses 1 to 3 wherein (B) is targeted to a folate receptor or a prostate specific membrane antigen (PSMA).

5. The conjugate of clause 2 wherein (B) is a folate.

6. The conjugate of clause 5 further comprising a therapeutic agent.

7. The conjugate of clause 5 or 6 wherein (B) is folate.

8. The conjugate of clause 5 having the formula

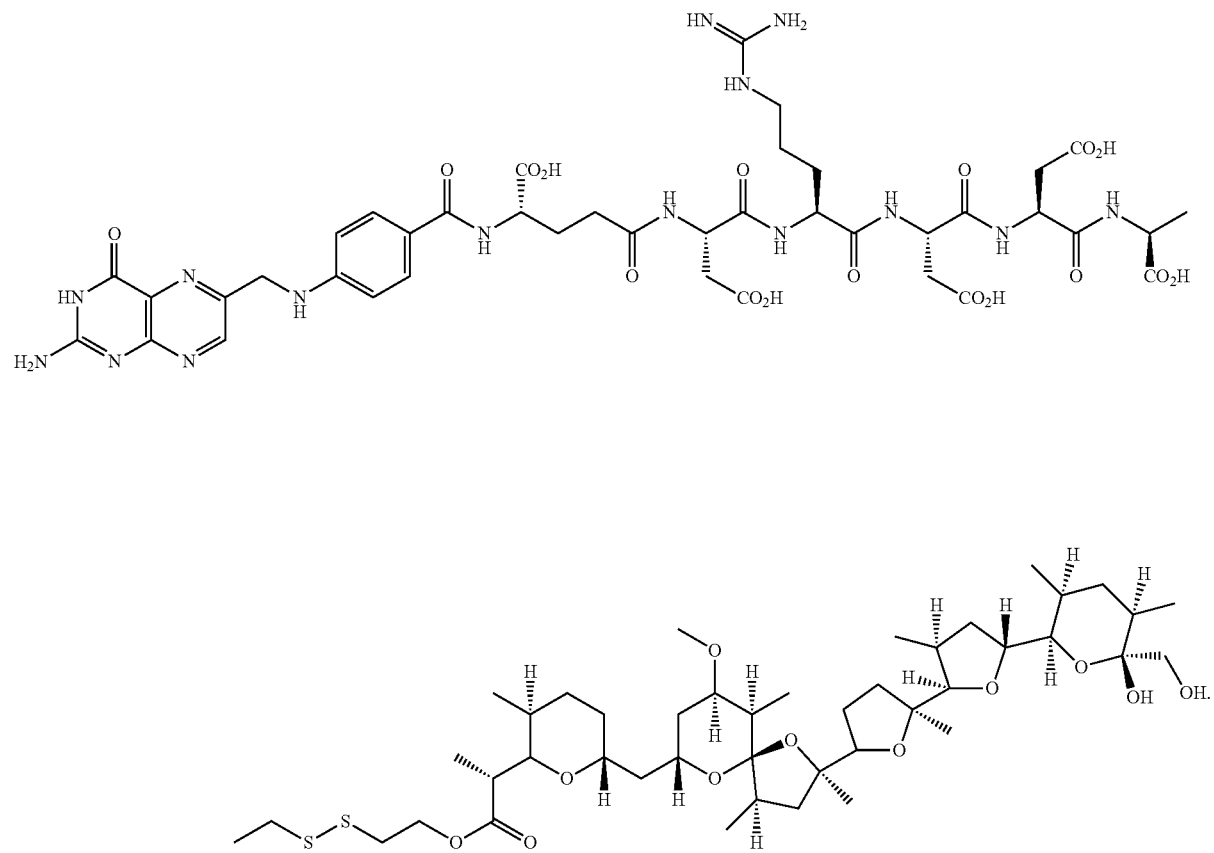

9. The conjugate of clause 5 having the formula
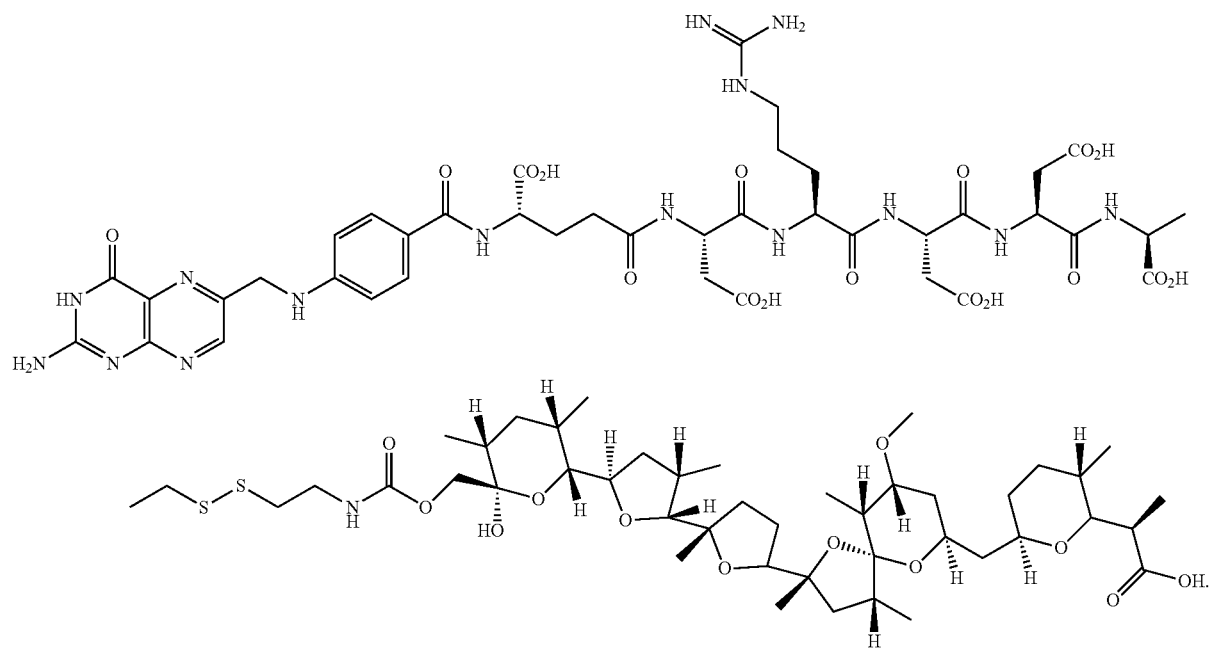
10. The conjugate of clause 6 having the formula
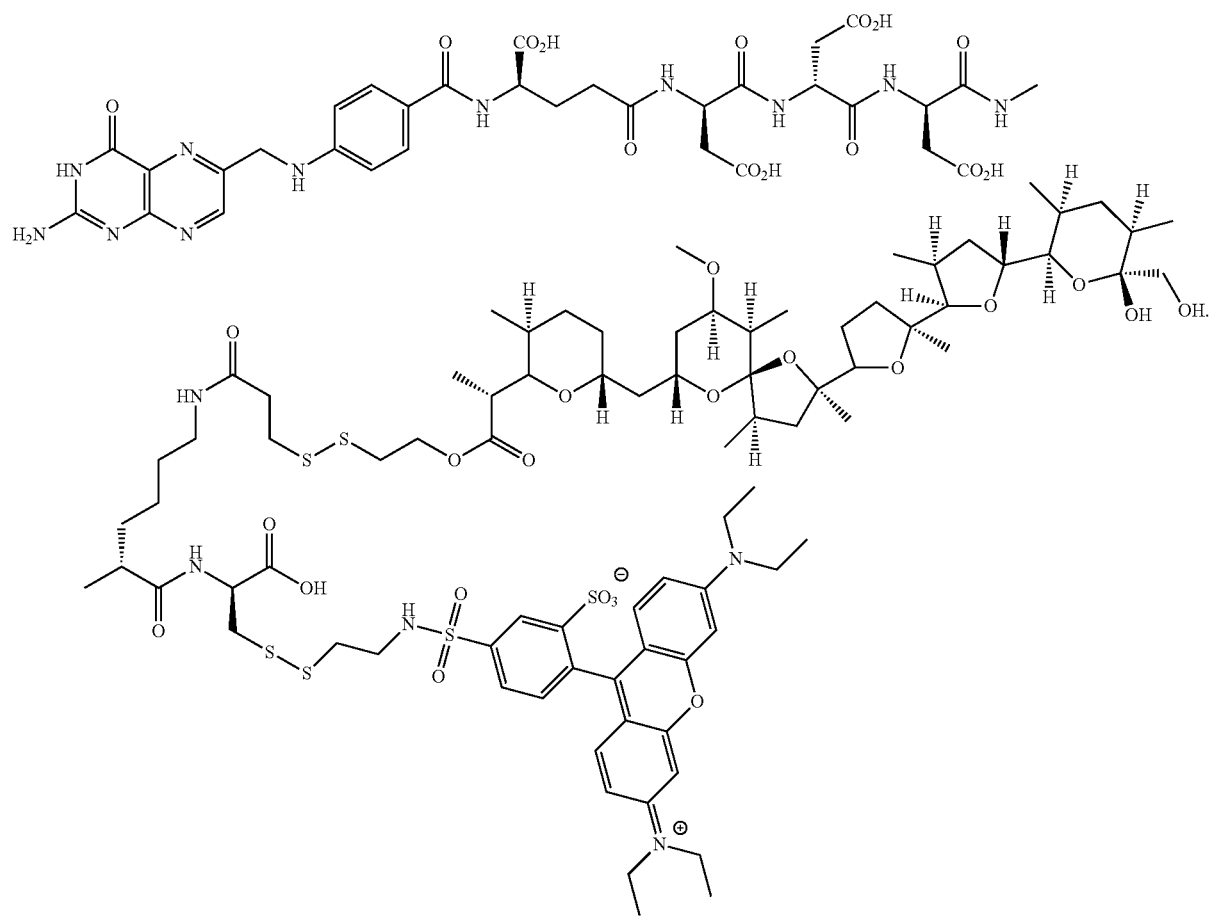

11. The conjugate of any one of clauses 1 to 4 wherein (B) is a PSMA binding ligand;

12. The conjugate of clause 11 further comprising a therapeutic agent or an imaging agent.

13. The conjugate of clause 11 or 12 wherein the PSMA binding ligand is 2-[3-(1-carboxy-2-mercaptoethyl)ureido]pentanedioic acid (MUPA) or 2-[3-(1,3-dicarboxypropyl)ureido]pentanedioic acid (DUPA).

14. The conjugate of clause 13 having the formula

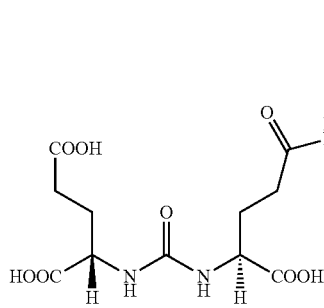
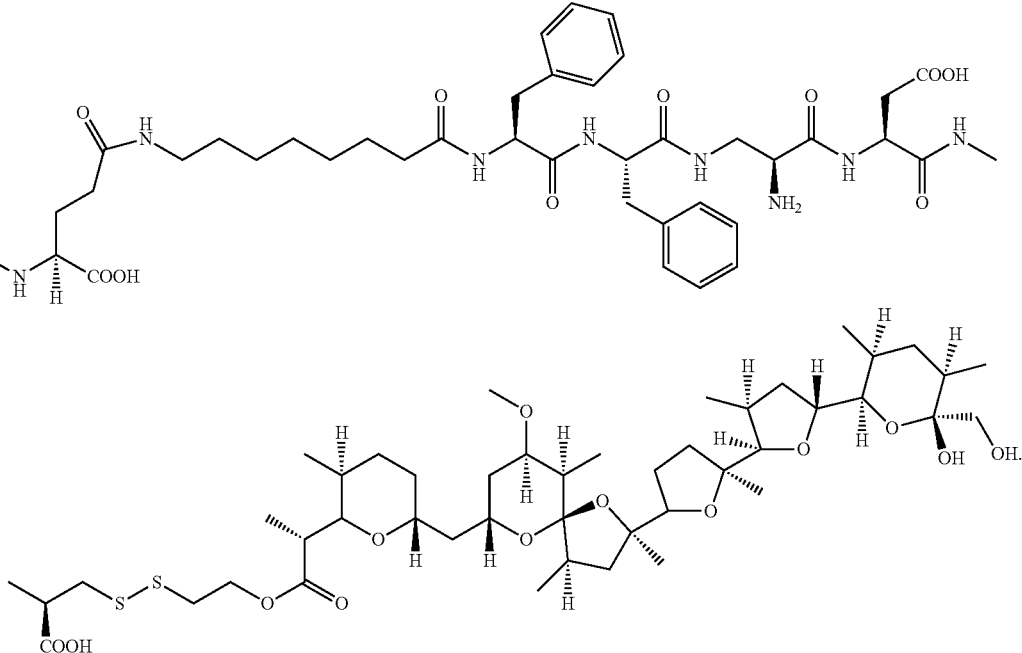

15. The conjugate of any of the preceding clauses 3-4, 6-7 or 12-13 wherein the therapeutic agent comprises a low molecular weight drug, a polypeptide, a peptide, an oligonucleotide, a nucleotide, an siRNA, an iRNA, a microRNA, a ribozyme, an antisense oligonucleotide, a protein, a glycoprotein, an antibody, an antigen, a synthetic amino acid, an aptamer, an oligosaccharide, or a polysaccharide.

16. The conjugate of clause 15 wherein the therapeutic agent is siRNA, miRNA or iRNA.

17. The conjugate of clause 15 wherein the therapeutic agent comprises a low molecular weight drug.

18. The conjugate of clause 15 wherein the therapeutic agent comprises a peptide or a synthetic amino acid.

19. The conjugate of clause 15 wherein the therapeutic agent comprises a low molecular weight chemotherapeutic agent.

20. The conjugate of clause 19 wherein the therapeutic agent comprises a taxane or an analog thereof, a *vinca* alkaloid or an analog thereof, camptothecin or an analog thereof, a tubulysin or an analog thereof, or doxorubicin or an analog thereof.

21. The conjugate of clause 15 wherein the therapeutic agent comprises a low molecular weight anti-inflammatory agent.

22. The conjugate of clause 15 wherein the therapeutic agent comprises a lipophilic anti-inflammatory steroid.

23. The conjugate of clause 3 or 12 comprising an imaging agent.

24. The conjugate of clause 23 wherein the imaging agent comprises a fluorescent dye.

25. A conjugate of any of the preceding clauses wherein (A) is an inhibitor of the $Na^+/H^+$ exchanger.

26. The conjugate of clause 25 further comprising an ionophore wherein the ionophore couples efflux of protons ($H^+$ ions) to influx of potassium ions ($K^+$ ions).

27. The conjugate of clause 25 wherein the inhibitor is amiloride or HOE 694.

28. The conjugate of any of clauses 25-27 wherein the inhibitor is amiloride.

29. The conjugate of any of the preceding clauses 1-7, 11-13, 15-24 and 26-28 wherein the ionophore (A) is selected from the group consisting of nigericin or salinomycin.

30. The conjugate of clause 29 wherein the ionophore is nigericin.

31. The conjugate of any of clauses 1-7, 11-13 and 15-30 wherein (L) comprises a chain of about 7 to about 45 atoms.

32. A pharmaceutical composition comprising the conjugate of any of clauses 1-31, and 15-22 and further comprising at least one pharmaceutically acceptable carrier or excipient.

33. A pharmaceutical composition comprising the conjugate as described in any of clauses 3, 12 and 15-22 further comprising an additional therapeutic agent.

34. A method of increasing the endosomal accumulation and escape of a therapeutic agent, or an imaging agent comprising the step of administering with the therapeutic agent or the imaging agent an effective amount of a ligand-ionophore conjugate wherein the ionophore couples efflux of protons ($H^+$ ions) to influx of potassium ions ($K^+$ ions) and wherein the therapeutic agent or the imaging agent is targeted to a cell-surface receptor.

35. The method of clause 34 wherein the ionophore is selected from the group consisting of nigericin or salinomycin.

36. The method of clause 35 wherein the ionophore is nigericin.

37. The method of any of clauses 34-36 wherein the imaging agent or the therapeutic agent is not linked to the conjugate.

38. The method of any of clauses 34-36 wherein the imaging agent or the therapeutic agent is linked to the conjugate.

39. The method of clause 37 or 38 wherein the imaging agent or the therapeutic agent is targeted to the same receptor as the ligand-ionophore conjugate.

40. The method of clause 37 or 38 wherein the ligand-ionophore conjugate is the conjugate of any of clauses 1-2, 4 and 29-31.

41. The method of clause 39 wherein the ligand-ionophore conjugate is a conjugate of formula (B)-(L)-(A) and further comprises the imaging agent or the therapeutic agent, covalently linked to (L) and wherein the therapeutic agent or the imaging agent is as described in any of clauses 3 or 15-24.

42. The method of any of clauses 34-41 wherein the cell-surface receptor targeted by the ligand-ionophore conjugate is the folate receptor or the prostate specific membrane antigen (PSMA).

43. The method of clause 42 wherein the cell-surface receptor targeted by the ligand-ionophore conjugate is the folate receptor.

44. The method of clause 42 wherein the cell-surface receptor targeted by the ligand-ionophore conjugate is PSMA.

45. The method of clause 43 or 44 wherein the therapeutic agent or the imaging agent is targeted to a cancer or a site of inflammation.

46. The method of clause 45 wherein the cancer is selected from the group consisting of ovarian, lung, breast, prostate, endometrial, brain, kidney and colon cancer.

47. The method of clause 46 wherein the cancer is lung cancer.

48. The method of clause 46 wherein the cancer is ovarian cancer.

49. The method of clause 45 wherein the therapeutic agent or imaging agent is targeted to a site of inflammatory disease.

50. The method of clause 49 wherein the inflammatory disease is selected from the group consisting of rheumatoid arthritis, osteoarthritis, atherosclerosis, diabetes, graft-versus-host disease, multiple sclerosis, osteomyelitis, psoriasis, Sjögren's syndrome, lupus erythematosus, Crohn's disease, and ulcerative colitis.

51. The method of clause 42 wherein the cell-surface receptor targeted by the ligand-ionophore conjugate is the prostate specific membrane antigen (PSMA).

52. The method of clause 51 wherein the ligand-ionophore conjugate is the conjugate described in any of clauses 11-24 and 29-31.

53. The method of clause 51 or 52 wherein the targeted cell-surface receptor is over-expressed PSMA.

54. The method of clause 53 wherein the therapeutic agent or the imaging agent is targeted to a malignant prostate cell population.

55. The method of any of clauses 34-54 comprising the administration of an inhibitor of the $Na^+/H^+$ exchanger (antiporter).

56. The method of clause 55 wherein the inhibitor of the $Na^+/H^+$ exchanger (antiporter) is amiloride or HOE 694.

57. The method of clause 55 or 56 wherein the inhibitor of the $Na^+/H^+$ exchanger (antiporter) is conjugated to the ligand.

58. The method of clause 55 or 56 wherein the inhibitor of the $Na^+/H^+$ exchanger (antiporter) is covalently linked to the ligand-ionophore conjugate and is releasable.

59. The method of any of clauses 34-58 wherein the imaging agent or the therapeutic agent is administered as a liposome, dendrimer or large molecular weight polymer complex in a targeted form.

60. The method of any of clauses 34-59 wherein the imaging agent or the therapeutic agent comprises an anti-cancer agent, an anti-inflammatory agent, a radionuclide, or a fluorescent dye.

61. The method of clause 60 wherein the therapeutic agent comprises a *vinca* alkaloid, doxorubicin, an antifolate or a corticosteroid.

62. Use of a folate-targeted ligand-ionophore conjugate as described in any of clauses 5-10, 15-20, 23-24 and 29-31 for the imaging or treatment of a cancer that expresses or overexpresses the folate receptor.

63. Use of a folate-targeted ligand-ionophore conjugate as described in any of clauses 5-10, 15-20, 23-24 and 29-31 for the manufacture of an agent for use in a method for imaging or treatment of a cancer that expresses or overexpresses the folate receptor.

64. An agent for use in imaging or treatment of a cancer that expresses or overexpresses the folate receptor, comprising a folate-targeted ligand-ionophore conjugate as described in any of clauses 5-10, 15-20, 23-24 and 29-31.

65. A method of using an effective amount of a folate-targeted ligand-ionophore conjugate as described in any of clauses 5-10, 15-20, 23-24 and 29-31 in a method for imaging or treatment of a cancer, that expresses or overexpresses the folate receptor, in a subject in need thereof.

66. Use of a folate-targeted ligand-ionophore conjugate as described in any of clauses 5-10, 15-18, 21-24 and 29-31 for imaging or treatment of an inflammatory disease at a site of inflammation.

67. Use of a folate-targeted ligand-ionophore conjugate as described in any of clauses 5-10, 15-18, 21-24 and 29-31 for the manufacture of an agent for use in a method for imaging or treatment of an inflammatory disease at a site of inflammation.

68. An agent for use in imaging or treatment of an inflammatory disease, comprising a folate-targeted ligand-ionophore conjugate as described in any of clauses 5-10, 15-18, 21-24 and 29-31.

69. A method of using an effective amount of a folate-targeted ligand-ionophore conjugate as described in any of clauses 5-10, 15-18, 21-24 and 29-31 for imaging or treatment of an inflammatory disease in a subject in need thereof.

70. Use of a PSMA-targeting ligand-ionophore conjugate as described in any of clauses 11-14, 15-20, 23-24 and 29-31 for the imaging or treatment of a cancer that expresses or overexpresses PSMA.

71. Use of a PSMA-targeting ligand-ionophore conjugate as described in any of clauses 11-14, 15-20, 23-24 and 29-31 for the manufacture of an agent for use in a method for imaging or treatment of a cancer that expresses or overexpresses PSMA.

72. An agent for use in imaging or treatment of a cancer that expresses or overexpresses PSMA, comprising a folate-targeted ligand-ionophore conjugate as described in any of clauses 11-14, 15-20, 23-24 and 29-31.

73. A method of using an effective amount of a folate-targeted ligand-ionophore conjugate as described in any of clauses 12-13, 15-20, 23-24 and 29-31 in a method for imaging or treatment of a cancer, that expresses or overexpresses PSMA, in a subject in need thereof.

74. Use of a folate-targeted ligand-ionophore conjugate as described in any of clauses 5-10, 15-18, 21-24 and 29-31 in association with a therapeutic agent or an imaging agent wherein the conjugate is internalized by endocytosis.

75. Use of a folate-targeted ligand-ionophore conjugate as described in any of clauses 5-10, 15-18, 21-24 and 29-31 for the manufacture of an agent for use in a method for imaging or treatment of a cancer, for use in association with a therapeutic agent, or an imaging agent that is internalized by endocytosis.

76. An agent for use in imaging or treatment of a cancer in association with a therapeutic agent, or an imaging agent that is internalized by endocytosis, wherein the agent comprises a folate-targeted ligand-ionophore conjugate as described in any of clauses 5-10, 15-18, 21-24 and 29-31.

77. A method of using an effective amount of a folate-targeted ligand-ionophore conjugate as described in any of clauses 5-10, 15-18, 21-24 and 29-31 in a method for imaging or treatment of a cancer in association with a therapeutic agent, or an imaging agent that is internalized by endocytosis.

78. Use of a folate-targeted ligand-ionophore conjugate as described in any of clauses 5-10, 15-18, 21-24 and 29-31 in association with a therapeutic agent, or an imaging agent that is internalized by endocytosis for imaging or treating an inflammatory disease at a site of inflammation.

79. Use of a folate-targeted ligand-ionophore conjugate as described in any of clauses 5-10, 15-18, 21-24 and 29-31 for the manufacture of an agent for use in a method for imaging or treatment of an inflammatory disease in association with a therapeutic agent, or an imaging agent that is internalized by endocytosis.

80. An agent for use in imaging or treatment of an inflammatory disease in association with a therapeutic agent, or an imaging agent that is internalized by endocytosis, wherein the agent comprises a folate-targeted ligand-ionophore conjugate as described in any of clauses 5-10, 15-18, 21-24 and 29-31.

81. A method of using an effective amount of a folate-targeted ligand-ionophore conjugate as described in any of clauses 5-10, 15-18, 21-24 and 29-31 in a method for imaging or treatment of an inflammatory disease in association with a therapeutic agent, or an imaging agent that is internalized by endocytosis.

82. Use of a PSMA-targeted ligand-ionophore conjugate as described in any of clauses 11-14, 15-20, 23-24 and 29-31 in association with a therapeutic agent, or an imaging agent that is internalized by endocytosis, for the imaging or treatment of a cancer that expresses or overexpresses PSMA.

83. Use of a PSMA-targeted ligand-ionophore conjugate as described in any of clauses 11-14, 15-20, 23-24 and 29-31 for the manufacture of an agent for use in a method for imaging or treatment, in association with a therapeutic agent, or an imaging agent that is internalized by endocytosis, of a cancer which expresses or overexpresses PSMA.

84. An agent for use in imaging or treatment of a cancer, in association with a therapeutic agent, or an imaging agent that is internalized by endocytosis, wherein the agent comprises a PSMA-targeting ligand-ionophore conjugate as described in any of clauses 11-14, 15-20, 23-24 and 29-31.

85. A method of using an effective amount of a PSMA-targeting ligand-ionophore conjugate as described in any of clauses 11-14, 15-20, 23-24 and 29-31 in a method for imaging or treatment of a cancer that expresses or overexpresses PSMA, in association with a therapeutic agent, or an imaging agent that is internalized by endocytosis.

DETAILED DESCRIPTION OF ILLUSTRATIVE EMBODIMENTS

Figure 1A:
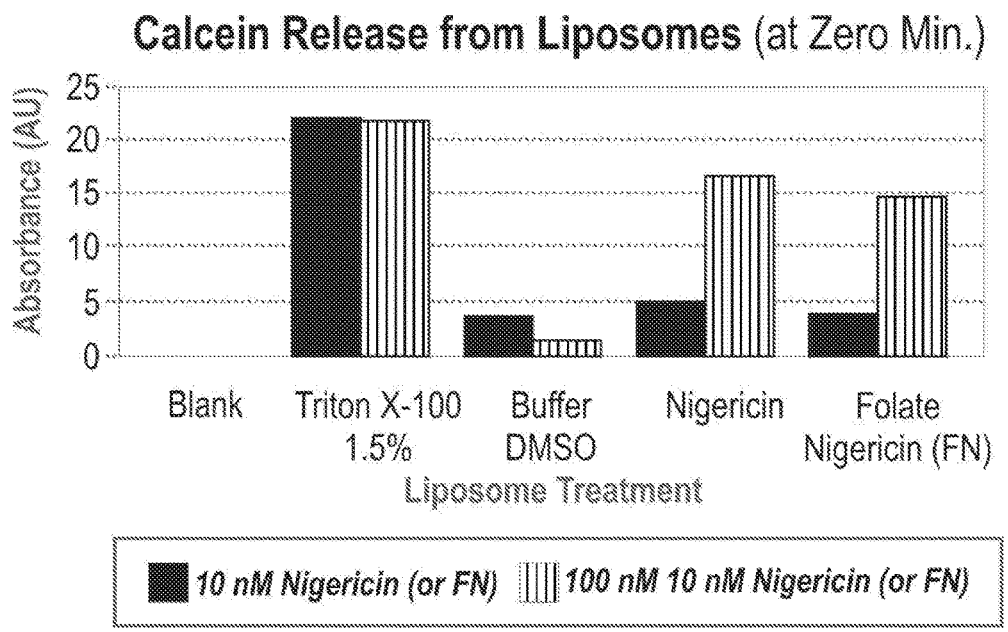
FIG. 1A shows a plot of absorption maximal intensity of released calcein dye from multilamellar liposomes with a high sodium ion content that were treated using either (i) Triton X-100 surfactant, (ii) tripotassium phosphate buffer with DMSO, (iii) the same buffer as (ii) with the addition of 10 mM or 100 mM nigericin, or (iv) the same buffer as (ii) with the addition of 10 mM or 100 mM folate nigericin ester conjugate

Several embodiments of the invention are described by the following enumerated clauses and any combination of these embodiments with the embodiments described in this Detailed Description section is contemplated.

1. A conjugate comprising:
   a ligand (B) targeted to a cell-surface receptor;
   a linker (L); and
   one or more ionophores (A) each of which couples efflux of protons ($H^+$ ions) to influx of potassium ions ($K^+$ ions);
   wherein (L) comprises at least one releasable linker; (B) is covalently linked to (L); and each (A) is covalently linked to (L).

2. The conjugate of clause 1 wherein (L) comprises at least one releasable linker.

3. The conjugate of clause 1 or 2 further comprising a therapeutic agent, and/or an imaging agent wherein the therapeutic agent or the imaging agent is covalently linked to (L).

4. The conjugate of any of clauses 1 to 3 wherein (B) is targeted to a folate receptor or a prostate specific membrane antigen (PSMA).

5. The conjugate of clause 2 wherein (B) is a folate.

6. The conjugate of clause 5 further comprising a therapeutic agent.

7. The conjugate of clause 5 or 6 wherein (B) is folate.

8. The conjugate of clause 5 having the formula

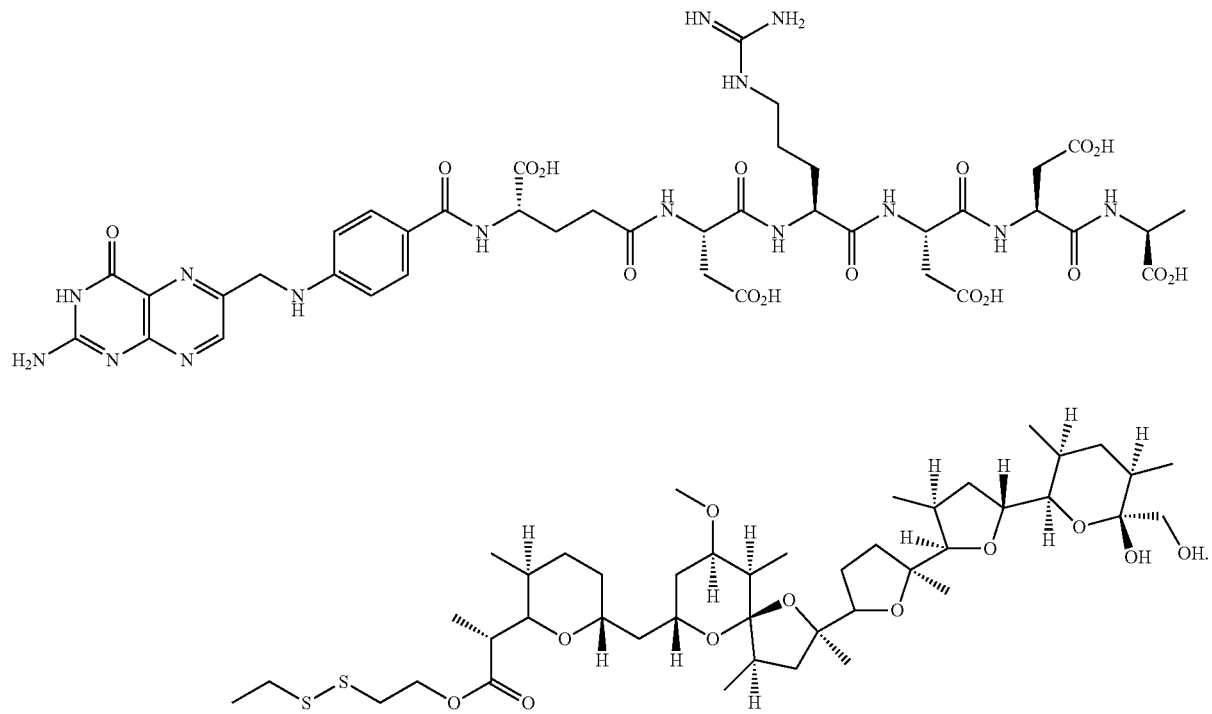

9. The conjugate of clause 5 having the formula

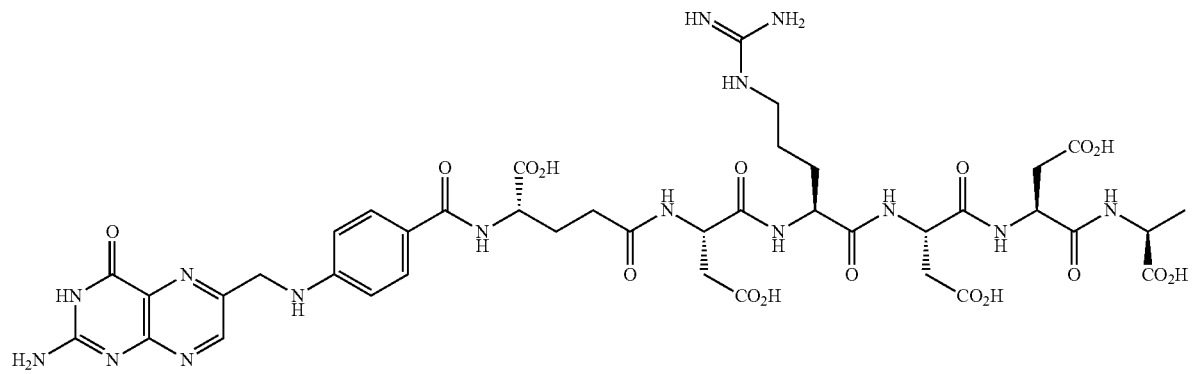

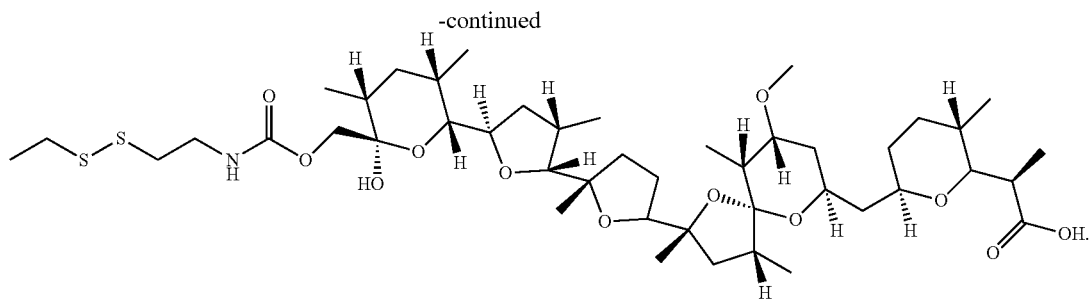

10. The conjugate of clause 6 having the formula

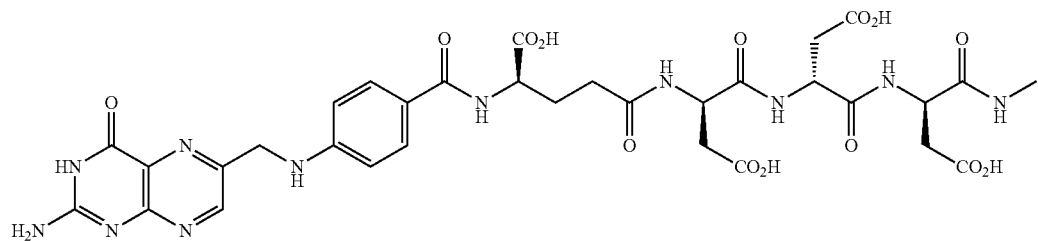

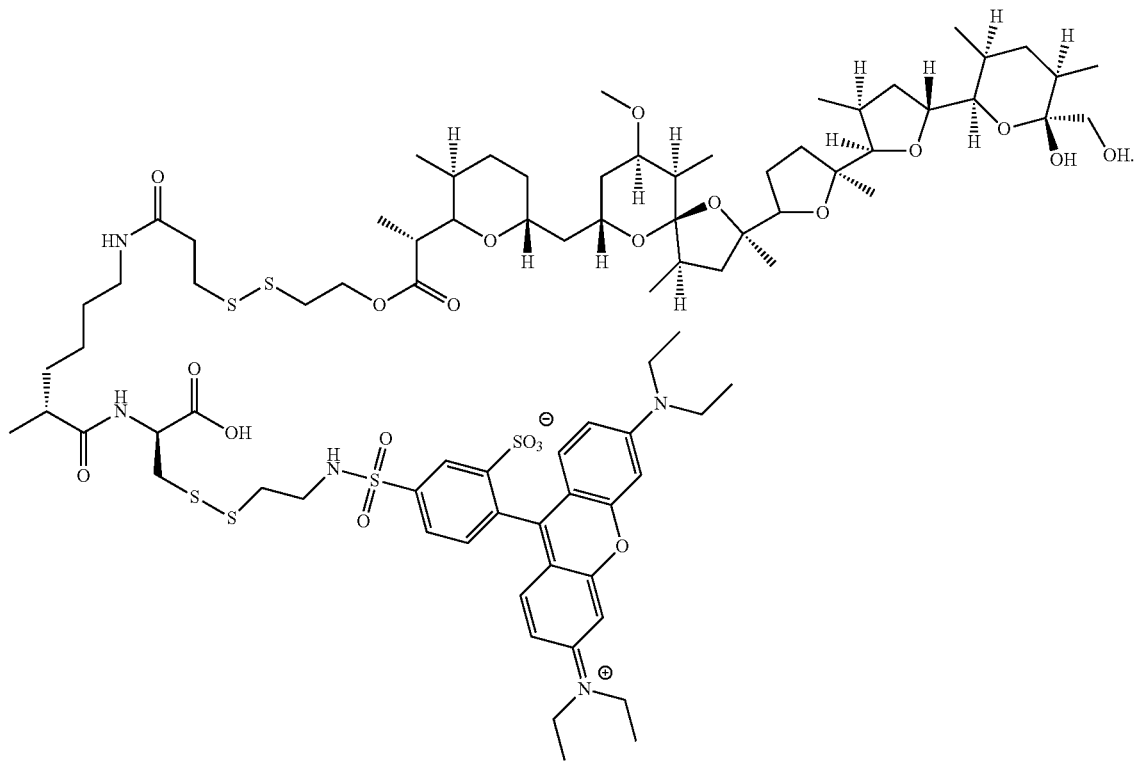

11. The conjugate of any one of clauses 1 to 4 wherein (B) is a PSMA binding ligand;

12. The conjugate of clause 11 further comprising a therapeutic agent or an imaging agent.

13. The conjugate of clause 11 or 12 wherein the PSMA binding ligand is 2-[3-(1-carboxy-2-mercaptoethyl)ureido] pentanedioic acid (MUPA) or 2-[3-(1,3-dicarboxypropyl) ureido]pentanedioic acid (DUPA).

14. The conjugate of clause 13 having the formula

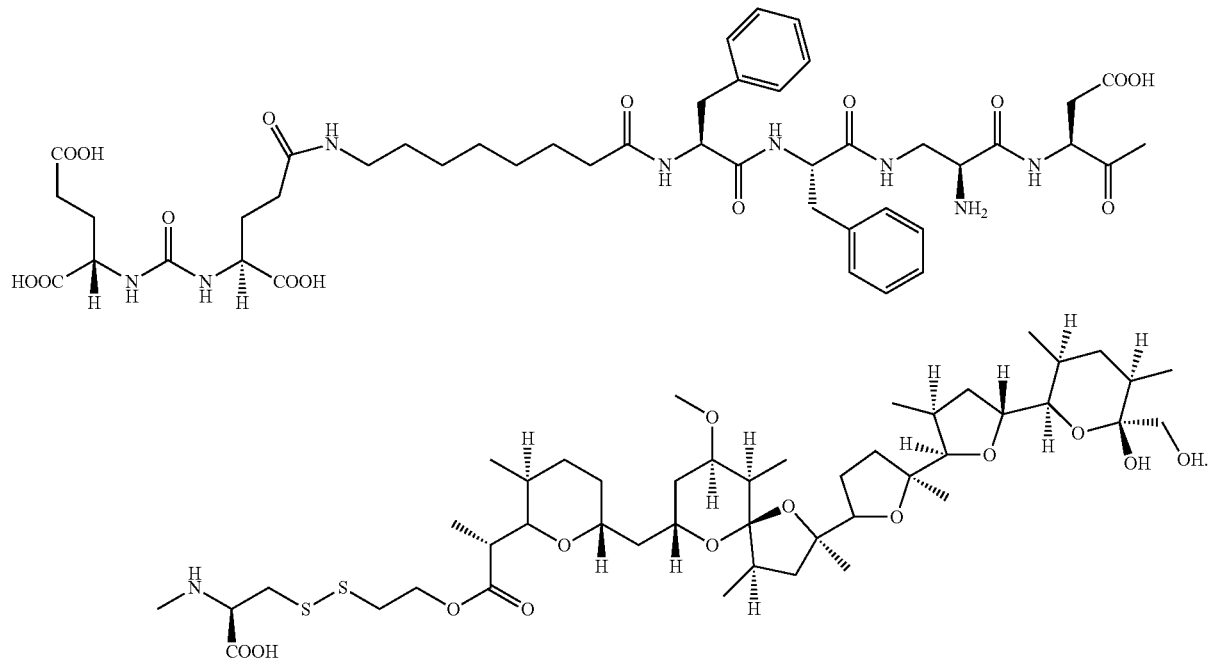

15. The conjugate of any of the preceding clauses 3-4, 6-7 or 12-13 wherein the therapeutic agent comprises a low molecular weight drug, a polypeptide, a peptide, an oligonucleotide, a nucleotide, an siRNA, an iRNA, a microRNA, a ribozyme, an antisense oligonucleotide, a protein, a glycoprotein, an antibody, an antigen, a synthetic amino acid, an aptamer, an oligosaccharide, or a polysaccharide.

16. The conjugate of clause 15 wherein the therapeutic agent is an siRNA, an miRNA, or an iRNA.

17. The conjugate of clause 15 wherein the therapeutic agent comprises a low molecular weight drug.

18. The conjugate of clause 15 wherein the therapeutic agent comprises a peptide or a synthetic amino acid.

19. The conjugate of clause 15 wherein the therapeutic agent comprises a low molecular weight chemotherapeutic agent.

20. The conjugate of clause 19 wherein the therapeutic agent comprises a taxane or an analog thereof, a *vinca* alkaloid or an analog thereof, camptothecin or an analog thereof, a tubulysin or an analog thereof, or doxorubicin or an analog thereof.

21. The conjugate of clause 15 wherein the therapeutic agent comprises a low molecular weight anti-inflammatory agent.

22. The conjugate of clause 15 wherein the therapeutic agent comprises a lipophilic anti-inflammatory steroid.

23. The conjugate of clause 3 or 12 comprising an imaging agent.

24. The conjugate of clause 23 wherein the imaging agent comprises a fluorescent dye.

25. A conjugate of any of the preceding clauses wherein (A) is an inhibitor of the $Na^+/H^+$ exchanger.

26. The conjugate of clause 25 further comprising an ionophore wherein the ionophore couples efflux of protons ($H^+$ ions) to influx of potassium ions ($K^+$ ions).

27. The conjugate of clause 25 wherein the inhibitor is amiloride or HOE 694.

28. The conjugate of any of clauses 25-27 wherein the inhibitor is amiloride.

29. The conjugate of any of the preceding clauses 1-7, 11-13, 15-24 and 26-28 wherein the ionophore (A) is selected from the group consisting of nigericin or salinomycin.

30. The conjugate of clause 29 wherein the ionophore is nigericin.

31. The conjugate of any of clauses 1-7, 11-13 and 15-30 wherein (L) comprises a chain of about 7 to about 45 atoms.

32. A pharmaceutical composition comprising the conjugate of any of clauses 1-31, and 15-22 and further comprising at least one pharmaceutically acceptable carrier or excipient.

33. A pharmaceutical composition comprising the conjugate as described in any of clauses 3, 12 and 15-22 further comprising an additional therapeutic agent.

34. A method of increasing the endosomal accumulation and escape of a therapeutic agent, or an imaging agent comprising the step of administering with the therapeutic agent or the imaging agent an effective amount of a ligand-ionophore conjugate wherein the ionophore couples efflux of protons ($H^+$ ions) to influx of potassium ions ($K^+$ ions) and wherein the therapeutic agent or the imaging agent is targeted to a cell-surface receptor.

35. The method of clause 34 wherein the ionophore is selected from the group consisting of nigericin or salinomycin.

36. The method of clause 35 wherein the ionophore is nigericin.

37. The method of any of clauses 34-36 wherein the imaging agent or the therapeutic agent is not linked to the conjugate.

38. The method of any of clauses 34-36 wherein the imaging agent or the therapeutic agent is linked to the conjugate.

39. The method of clause 37 or 38 wherein the imaging agent or the therapeutic agent is targeted to the same receptor as the ligand-ionophore conjugate.

40. The method of clause 37 or 38 wherein the ligand-ionophore conjugate is the conjugate of any of clauses 1-2, 4 and 29-31.

41. The method of clause 39 wherein the ligand-ionophore conjugate is a conjugate of formula (B)-(L)-(A) and further comprises the imaging agent or the therapeutic agent, covalently linked to (L) and wherein the therapeutic agent or the imaging agent is as described in any of clauses 3 or 15-24.

42. The method of any of clauses 34-41 wherein the cell-surface receptor targeted by the ligand-ionophore conjugate is the folate receptor or the prostate specific membrane antigen (PSMA).

43. The method of clause 42 wherein the cell-surface receptor targeted by the ligand-ionophore conjugate is the folate receptor.

44. The method of clause 42 wherein the cell-surface receptor targeted by the ligand-ionophore conjugate is PSMA.

45. The method of clause 43 or 44 wherein the therapeutic agent or the imaging agent is targeted to a cancer or a site of inflammation.

46. The method of clause 45 wherein the cancer is selected from the group consisting of ovarian, lung, breast, prostate, endometrial, brain, kidney and colon cancer.

47. The method of clause 46 wherein the cancer is lung cancer.

48. The method of clause 46 wherein the cancer is ovarian cancer.

49. The method of clause 45 wherein the therapeutic agent or imaging agent is targeted to a site of inflammatory disease.

50. The method of clause 49 wherein the inflammatory disease is selected from the group consisting of rheumatoid arthritis, osteoarthritis, atherosclerosis, diabetes, graft-versus-host disease, multiple sclerosis, osteomyelitis, psoriasis, Crohn's disease, Sjögren's syndrome, lupus erythematosus, and ulcerative colitis.

51. The method of clause 42 wherein the cell-surface receptor targeted by the ligand-ionophore conjugate is the prostate specific membrane antigen (PSMA).

52. The method of clause 51 wherein the ligand-ionophore conjugate is the conjugate described in any of clauses 11-24 and 29-31.

53. The method of clause 51 or 52 wherein the targeted cell-surface receptor is over-expressed PSMA.

54. The method of clause 53 wherein the therapeutic agent or the imaging agent is targeted to a malignant prostate cell population.

55. The method of any of clauses 34-54 comprising the administration of an inhibitor of the $Na^+/H^+$ exchanger (antiporter).

56. The method of clause 55 wherein the inhibitor of the $Na^+/H^+$ exchanger (antiporter) is amiloride or HOE 694.

57. The method of clause 55 or 56 wherein the inhibitor of the $Na^+/H^+$ exchanger (antiporter) is conjugated to the ligand.

58. The method of clause 55 or 56 wherein the inhibitor of the $Na^+/H^+$ exchanger (antiporter) is covalently linked to the ligand-ionophore conjugate and is releasable.

59. The method of any of clauses 34-58 wherein the imaging agent or the therapeutic agent is administered as a liposome, dendrimer or large molecular weight polymer complex in a targeted form.

60. The method of any of clauses 34-59 wherein the imaging agent or the therapeutic agent comprises an anti-cancer agent, an anti-inflammatory agent, a radionuclide, or a fluorescent dye.

61. The method of clause 60 wherein the therapeutic agent comprises a *vinca* alkaloid, doxorubicin, an antifolate or a corticosteroid.

62. Use of a folate-targeted ligand-ionophore conjugate as described in any of clauses 5-10, 15-20, 23-24 and 29-31 for the imaging or treatment of a cancer that expresses or overexpresses the folate receptor.

63. Use of a folate-targeted ligand-ionophore conjugate as described in any of clauses 5-10, 15-20, 23-24 and 29-31 for the manufacture of an agent for use in a method for imaging or treatment of a cancer that expresses or overexpresses the folate receptor.

64. An agent for use in imaging or treatment of a cancer that expresses or overexpresses the folate receptor, comprising a folate-targeted ligand-ionophore conjugate as described in any of clauses 5-10, 15-20, 23-24 and 29-31.

65. A method of using an effective amount of a folate-targeted ligand-ionophore conjugate as described in any of clauses 5-10, 15-20, 23-24 and 29-31 in a method for imaging or treatment of a cancer, that expresses or overexpresses the folate receptor, in a subject in need thereof.

66. Use of a folate-targeted ligand-ionophore conjugate as described in any of clauses 5-10, 15-18, 21-24 and 29-31 for imaging or treatment of an inflammatory disease at a site of inflammation.

67. Use of a folate-targeted ligand-ionophore conjugate as described in any of clauses 5-10, 15-18, 21-24 and 29-31 for the manufacture of an agent for use in a method for imaging or treatment of an inflammatory disease at a site of inflammation.

68. An agent for use in imaging or treatment of an inflammatory disease, comprising a folate-targeted ligand-ionophore conjugate as described in any of clauses 5-10, 15-18, 21-24 and 29-31.

69. A method of using an effective amount of a folate-targeted ligand-ionophore conjugate as described in any of clauses 5-10, 15-18, 21-24 and 29-31 for imaging or treatment of an inflammatory disease in a subject in need thereof.

70. Use of a PSMA-targeting ligand-ionophore conjugate as described in any of clauses 11-14, 15-20, 23-24 and 29-31 for the imaging or treatment of a cancer that expresses or overexpresses PSMA.

71. Use of a PSMA-targeting ligand-ionophore conjugate as described in any of clauses 11-14, 15-20, 23-24 and 29-31 for the manufacture of an agent for use in a method for imaging or treatment of a cancer that expresses or overexpresses PSMA.

72. An agent for use in imaging or treatment of a cancer that expresses or overexpresses PSMA, comprising a folate-targeted ligand-ionophore conjugate as described in any of clauses 11-14, 15-20, 23-24 and 29-31.

73. A method of using an effective amount of a folate-targeted ligand-ionophore conjugate as described in any of clauses 12-13, 15-20, 23-24 and 29-31 in a method for imaging or treatment of a cancer, that expresses or overexpresses PSMA, in a subject in need thereof.

74. Use of a folate-targeted ligand-ionophore conjugate as described in any of clauses 5-10, 15-18, 21-24 and 29-31 in association with a therapeutic agent or an imaging agent wherein the conjugate is internalized by endocytosis.

75. Use of a folate-targeted ligand-ionophore conjugate as described in any of clauses 5-10, 15-18, 21-24 and 29-31 for the manufacture of an agent for use in a method for imaging 76. An agent for use in imaging or treatment of a cancer in association with a therapeutic agent, or an imaging agent that is internalized by endocytosis, wherein the agent comprises a folate-targeted ligand-ionophore conjugate as described in any of clauses 5-10, 15-18, 21-24 and 29-31.

77. A method of using an effective amount of a folate-targeted ligand-ionophore conjugate as described in any of clauses 5-10, 15-18, 21-24 and 29-31 in a method for imaging or treatment of a cancer in association with a therapeutic agent, or an imaging agent that is internalized by endocytosis.

78. Use of a folate-targeted ligand-ionophore conjugate as described in any of clauses 5-10, 15-18, 21-24 and 29-31 in association with a therapeutic agent, or an imaging agent that is internalized by endocytosis for imaging or treating an inflammatory disease at a site of inflammation.

79. Use of a folate-targeted ligand-ionophore conjugate as described in any of clauses 5-10, 15-18, 21-24 and 29-31 for the manufacture of an agent for use in a method for imaging or treatment of an inflammatory disease in association with a therapeutic agent, or an imaging agent that is internalized by endocytosis.

80. An agent for use in imaging or treatment of an inflammatory disease in association with a therapeutic agent, or an imaging agent that is internalized by endocytosis, wherein the agent comprises a folate-targeted ligand-ionophore conjugate as described in any of clauses 5-10, 15-18, 21-24 and 29-31.

81. A method of using an effective amount of a folate-targeted ligand-ionophore conjugate as described in any of clauses 5-10, 15-18, 21-24 and 29-31 in a method for imaging or treatment of an inflammatory disease in association with a therapeutic agent, or an imaging agent that is internalized by endocytosis.

82. Use of a PSMA-targeted ligand-ionophore conjugate as described in any of clauses 11-14, 15-20, 23-24 and 29-31 in association with a therapeutic agent, or an imaging agent that is internalized by endocytosis, for the imaging or treatment of a cancer that expresses or overexpresses PSMA.

83. Use of a PSMA-targeted ligand-ionophore conjugate as described in any of clauses 11-14, 15-20, 23-24 and 29-31 for the manufacture of an agent for use in a method for imaging or treatment, in association with a therapeutic agent, or an imaging agent that is internalized by endocytosis, of a cancer which expresses or overexpresses PSMA.

84. An agent for use in imaging or treatment of a cancer, in association with a therapeutic agent, or an imaging agent that is internalized by endocytosis, wherein the agent comprises a PSMA-targeting ligand-ionophore conjugate as described in any of clauses 11-14, 15-20, 23-24 and 29-31.

85. A method of using an effective amount of a PSMA-targeting ligand-ionophore conjugate as described in any of clauses 11-14, 15-20, 23-24 and 29-31 in a method for imaging or treatment of a cancer that expresses or overexpresses PSMA, in association with a therapeutic agent, or an imaging agent that is internalized by endocytosis.

As used herein, the term "conjugate" means the ligand-ionophore (ligand-ionophore means with or without a linker between the ligand and the ionophore) conjugate or a ligand-ionophore (ligand-ionophore means with or without a linker between the ligand and the ionophore) conjugate with a linked therapeutic agent or imaging agent, or a pharmaceutically acceptable salt of the conjugate, or a solvate thereof; and the conjugate may be present in solution or suspension in an ionized form, including a protonated form.

As used herein, the term "ionophore" also means a cluster of ionophores, for example, in a dendritic construct. Similarly, a therapeutic agent, or an imaging agent conjugated to the ligand-ionophore conjugate may be a cluster of agents, for example, in a dendritic construct.

As used herein, the term "releasable" means that the particular moiety is covalently linked to the linker (L) by a releasable linker.

As used herein, the terms drug, therapeutic agent, chemotherapeutic agent, etc. include analogs thereof which can be incorporated into a conjugate or administered separately, in targeted form.

As used herein the term "endocytosis" has its art-recognized meaning and includes several analogous processes, such as the process of PSMA internalization.

It will be appreciated that the therapeutic agent or the imaging agent may comprise an agent prepared by synthetic chemistry, an agent isolated from a natural source, a biologically synthesized agent, or a macromolecular structure such as a liposome or a dendrimer comprising the therapeutic agent, or the imaging agent.

The therapeutic agent can be any molecule capable of modulating or otherwise modifying cell function, including pharmaceutically active compounds. Therapeutic agents may be antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics and antidepressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives, or any other therapeutic agent known to a skilled artisan.

When a therapeutic agent is an anticancer agent, the therapeutic agent can be any drug known in the art which is cytotoxic, enhances tumor permeability, inhibits tumor cell proliferation, promotes apoptosis, decreases anti-apoptotic activity in tumor cells, enhances an endogenous immune response directed to the tumor cells, or is useful for treating a cancer.

Therapeutic agents suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and antifolates, such as methotrexate and aminopterin, busulfan, carboplatin, chlorambucil, cisplatin and other platinum compounds, taxanes, such as tamoxiphen, taxol, paclitaxel, paclitaxel derivatives, Taxotere™, and the like, maytansines and analogs and derivatives thereof, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, everolimus, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vincristine, vinblastine, and analogs and derivatives thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, doxorubicin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin.

When the therapeutic agent is a chemotherapeutic agent, it is selected from those which are, for example, cytotoxic themselves or can work to enhance tumor permeability, and are also suitable for use in the method of the invention in combination with the ligand-ionophore conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, aminopterin, any art-recognized antifolate, an everolimus, busulfan, carboplatin, chlorambucil, cisplatin and other platinum compounds, tamoxiphen, taxol, paclitaxel, paclitaxel derivatives, Taxotere™, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin.

When the therapeutic agent is an anti-inflammatory agent, it may comprise an anti-inflammatory steroid, a topically administered anti-inflammatory steroid, a water soluble anti-inflammatory steroid, a non-steroidal anti-inflammatory drug (NSAID), which also may be denoted as a non-steroidal anti-inflammatory agent (NSAIA) or as a non-steroidal anti-inflammatory medicine (NSAIM), or another drug useful in the treatment of rheumatoid arthritis or another autoimmune disease including an antiproliferative, immunomodulator or immunosuppressant agent.

When the therapeutic agent is an anti-inflammatory agent it may comprise a systemically administered (lipophilic) anti-inflammatory steroid. In one embodiment, the anti-inflammatory steroid is betamethasone, dexamethasone, flumethasone, methylprednisolone, paramethasone, prednisolone, prednisone, triamcinolone, hydrocortisone, or cortisone. In a further embodiment, the anti-inflammatory steroid is betamethasone.

When the therapeutic agent comprises a topically administered anti-inflammatory steroid, the anti-inflammatory steroid can be alcomethasone dipropionate, amcinonide, betamethasone dipropionate, betamethasone monopropionate, betamethasone 17-valerate, budesonide, budesonide disodium phosphate, ciclomethasone, clobetasol-17-propionate, clobetasone-17-butyrate, cortisone acetate, deprodone propionate, desonide, desoxymethasone, dexamethasone acetate, diflucortolone valerate, diflurasone diacetate, diflucortolone, difluprednate, flumetasone pivalate, flunisolide, fluocinolone acetonide acetate, fluocinonide, fluocortolone, fluocortolone caproate, fluocortolone hexanoate, fluocortolone pivalate, fluormetholone acetate, fluprednidene acetate, fluticasone propionate, halcinonide, halometasone, hydrocortisone acetate, hydrocortisone-17-butyrate, hydrocortisone-17-valerate, medrysone, methylprednisolone acetate, mometasone furoate, parametasone acetate, prednicarbate, prednisolone acetate, prednylidene, rimexolone, tixocortol pivalate, triamcinolone acetonide, triamcinolone alcohol or triamcinolone hexacetonide. In one embodiment, it is budesonide, flunisolide or fluticasone propionate.

When the therapeutic agent is an anti-inflammatory agent it may comprise a water soluble anti-inflammatory steroid. In one embodiment, the anti-inflammatory steroid can be betamethasone sodium phosphate, desonide sodium phosphate, dexamethasone sodium phosphate, hydrocortisone sodium phosphate, hydrocortisone sodium succinate, cortisone sodium phosphate, cortisone sodium succinate, methylprednisolone disodium phosphate, methylprednisolone sodium succinate, methylprednisone disodium phosphate, methylprednisone sodium succinate, prednisolone sodium phosphate, prednisolone sodium succinate, prednisone sodium phosphate, prednisone sodium succinate, prednisolamate hydrochloride, triamcinolone acetonide disodium phosphate or triamcinolone acetonide dipotassium phosphate. In one embodiment, the therapeutic agent is budesonide disodium phosphate.

When the therapeutic agent is an anti-inflammatory agent it can be a non-steroidal anti-inflammatory drug (NSAID), and the NSAID can comprise a propionic acid derivative such as, for example, ibuprofen, naproxen, fenoprofen, ketoprofen, flurbiprofen or oxaprozin; or the NSAID can comprise an acetic acid derivative, such as, for example, indomethacin, sulindac, etodolac or diclofenac; or the NSAID can comprise an oxicam derivative, such as, for example, piroxicam, meloxicam, tenoxicam, droxicam, lornoxicam or isoxicam; or the NSAID can comprise a fenamic acid derivative, such as, for example, mefenamic acid, meclofenamic acid, flufenamic acid or tolfenamic acid; or the NSAID can comprise a selective COX-2 (cyclooxygenase-2) inhibitor (coxib), such as, for example, celecoxib, rofecoxib, valdecoxib, parecoxib, lumiracoxib or etoricoxib.

When the therapeutic agent is an anti-inflammatory agent it can comprise a drug useful in the treatment of rheumatoid arthritis or another autoimmune disease including an antiproliferative, immunomodulator or immunosuppressant agent. In one embodiment the anti-inflammatory agent can comprise, for example, aspirin, methotrexate, sulfasalazine, D-penicillamine, nambumetone, aurothioglucose, auranofin, other gold-containing compound, colloidal gold, cyclosporin, tacrolimus, pimecrolimus or sirolimus.

When the therapeutic agent is a biologic, it may be for example, a polypeptide, a peptide, an oligonucleotide, a nucleotide, an siRNA, an iRNA, a microRNA, a ribozyme, an antisense oligonucleotide, a protein, a glycoprotein, an antibody, an antigen, a synthetic amino acid, an aptamer, an oligosaccaride, or a polysaccaride.

When the agent is an imaging agent, the agent may comprise a fluorescent agent, an X-ray contrast agent, such as for example iobitridol, a PET imaging agent, or a radionuclide, such as for example, an isotope of gallium, indium, copper, technitium or rhenium. Fluorescent agents include Oregon Green fluorescent agents, including but not limited to Oregon Green 488, Oregon Green 514, and the like, AlexaFluor fluorescent agents, including but not limited to AlexaFluor 488, AlexaFluor 647, and the like, fluorescein, and related analogs, BODIPY fluorescent agents, including but not limited to BODIPY Fl, BODIPY 505, and the like, rhodamine fluorescent agents, including but not limited to tetramethylrhodamine, and the like, DyLight fluorescent agents, including but not limited to DyLight 647, DyLight 680, DyLight 800, and the like, CW 800, Texas Red, phycoerythrin, and others.

The preparation and use of releasable linkers for releasing the "payload" is well documented. The conjugation of the ligand and ionophore, may utilize procedures which are analogous to those used for single or dual conjugation of a drug employing releasable linkers, as described, for example, inter alia, in WO 2003/097647, WO 2004/069159, WO 2006/012527, WO 2007/022493, WO 2007/022494, WO 2009/002993 WO 2010/033733 and WO 2010/045584. The disclosures of each of the foregoing patent applications are incorporated herein by reference. These same references also describe methods that can be used to link the therapeutic agent or the imaging agent to the ligand-ionophore conjugate, or to prepare separate ligand-therapeutic agent or ligand-imaging agent compounds.

Uses and preparation of PMSA targeting ligands and intermediates linked to ionophores useful for the instant invention are described, inter alia, in WO 2009/026177, WO 2010/045598 and WO 2011/106639. The disclosures of each of the foregoing patent applications are incorporated herein by reference. These same references also describe methods that can be used to link the therapeutic agent or the imaging agent to the ligand-ionophore conjugate, or to prepare separate ligand-therapeutic agent or ligand-imaging agent compounds. DUPA binds selectively to prostate-specific membrane antigen (Ligand-Targeted Delivery of Small Interfering RNAs to Malignant Cells and Tissues. Thomas, M., Kularatne, S. A., Qi, L., Kleindl, P., Leamon, C. P., Hansen, M. J., and Low, P. S. Ann. N.Y. Acad. Sci. 1175, 32-39 (2009)).

In an illustrative example, nigericin, an ionophore and hydrogen ion/potassium ion antiporter, containing free hydroxyl and carboxylic acid functional groups is chemically attached to a ligand through releasable linkers bound to the hydroxyl or carboxylic acid groups, as shown in the examples. In one illustrative example, in the folate-nigericin ester conjugate 1, a folate ligand is conjugated via a disulfide containing linker to nigericin through the carboxylic acid functional group. A similar conjugation method is used for the folate-S,S-nigericin-S,S-rhodamine dual conjugate. In another illustrative example, a folate ligand is conjugated via a disulfide linkage to the hydroxyl group to form the folate-nigericin conjugate 5.

Similarly, conjugation of the PMSA binding ligand 2-[3-(1,3-dicarboxypropyl)-ureido]pentanedioic acid (DUPA) via a disulfide containing linker to nigericin through the carboxylic acid functional group is shown in the Examples for the preparation of the DUPA-S,S-nigericin conjugate.

The invention described herein also includes pharmaceutical compositions comprising the ligand-ionophore conjugate described herein and further comprising at least one pharmaceutically acceptable carrier or excipient. The ligand-ionophore conjugate is preferably administered to the patient (i.e., subject in need thereof) parenterally, e.g., intradermally, subcutaneously, intramuscularly, intraperitoneally, intravenously, or intrathecally. Alternatively, the ligand-ionophore conjugate can be administered to a patient (e.g., human or animal) by other medically useful processes, such as by inhalation, nasal administration, buccal absorption, transdermal, rectal or vaginal suppository, per os (oral), and any effective dose and suitable dosage form, including prolonged release dosage forms, can be used.

Examples of parenteral dosage forms include aqueous solutions of the ligand-ionophore conjugate in an isotonic saline solution, a glucose solution or other well-known pharmaceutically acceptable liquid carriers such as liquid alcohols, glycols, esters, and amides or suspensions of liposomes. The parenteral dosage form in accordance with this invention can be in the form of a reconstitutable lyophilizate comprising the dose of the ligand-ionophore conjugate. In one embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

The ligand-ionophore conjugate can be administered to the patient prior to, after, or at the same time as the therapeutic agent, or imaging agent that is internalized by endocytosis, as determined by the relevant medical professional.

EXAMPLES

The following examples further illustrate specific embodiments of the invention; however, the following illustrative examples should not be interpreted in any way to limit the invention. Abbreviations used herein include: DCC, dicyclohexylcarbodiimide; Py, 2-pyridyl; RT, room temperature.

Preparative Examples

Preparation of Pyridyldisulfide Ethyl Ester of Nigericin

Nigericin sodium salt from AG scientific (36 mg) was stirred with 1N $HClO_4$ (0.5 mL) for an hour in $CHCl_3$ (0.5 mL), washed with water (2×25 mL), extracted with $CHCl_3$ (3×15 mL) and dried over anhyd.$Na_2SO_4$. The organic extract was filtered and evaporated to provide nigericin free acid in quantitative yield and it was used for esterification without further purification.

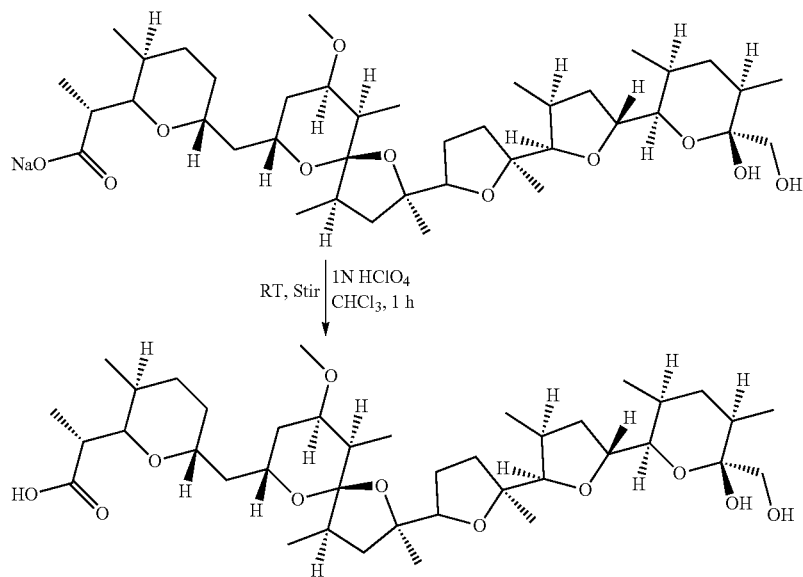

Nigericin free acid (30 mg), PyS-S(CH$_2$)$_2$OH (38 mg), DCC (17 mg) and pyrrolidino pyridine (6 mg) were dissolved in anhyd.CH$_2$Cl$_2$ (0.3 mL) and stirred under argon for overnight. Dicyclohexyl urea precipitates out from the reaction mixture as the reaction proceeds. Thin layer chromatography showed the appearance of a new product in the eluent (MeOH:CH$_2$Cl$_2$, 5:95) with R$_f$=0.3, below PyS-S(CH$_2$)$_2$OH.

The reaction mixture was dissolved in 0.5 mL CH$_2$Cl$_2$ and the product pyridyldisulfide ethyl ester of nigericin was purified by preparative thin layer chromatography using 5% MeOH:CH$_2$Cl$_2$ as eluent. The nigericin ester band over silica gel plate was cut and the silica gel was extracted with 2% MeOH:CH$_2$Cl$_2$ (100 mL) and filtered through Whatman filter paper. The organic extract was evaporated and the nigericin ester was separated from residual thin-layer-chro-

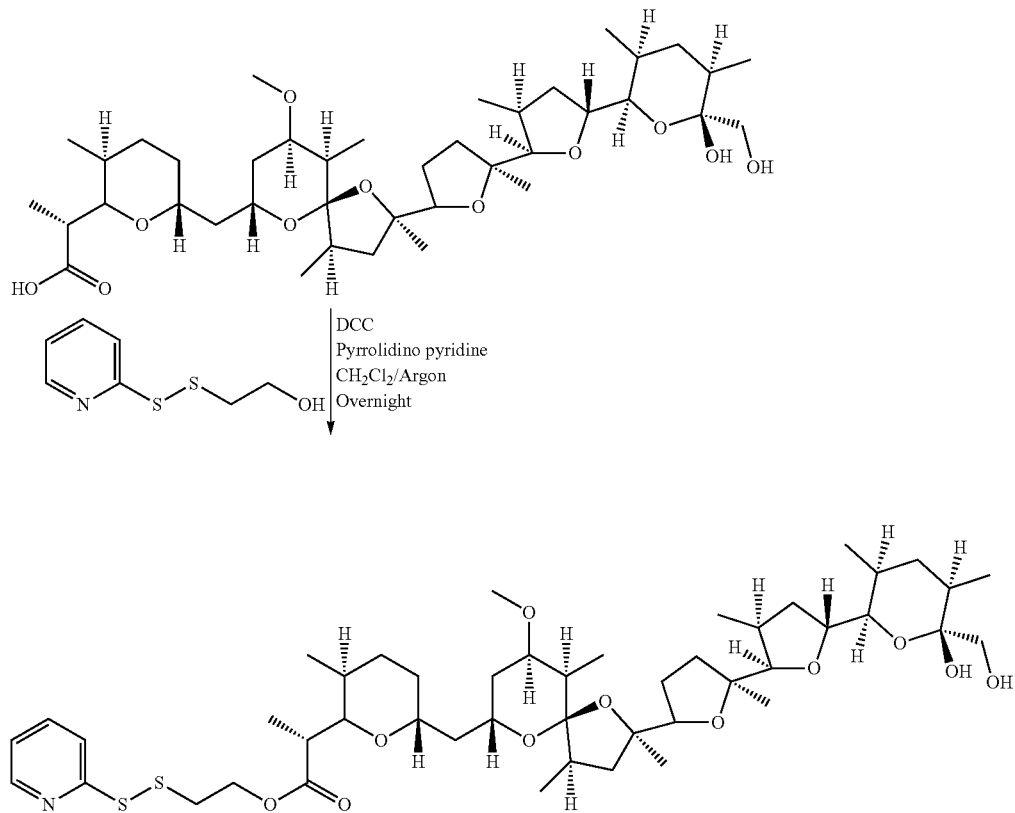

matography silica gel by filtration through a filter paper or by passing over a plug of silica gel using column chromatography.

The product, pyridyldisulfide ethyl ester of nigericin, is obtained in 54% (20 mg) yield with LC-MS (10-100% MeOH, pH=7.0, 12 min run) showing a peak at $R_t$=8.94 min for $(M+NH_4^+)$=911.66 where M=molecular mass of the nigericin ester.

Preparation of Folate-Nigericin Ester Conjugate 1

The EC-119 linker may be obtained, for example, as described in Example 1 at page 45 of WO 2007/022493, incorporated herein by reference. Pyridyldisulfide ethyl ester of nigericin (5 mg) and EC-119 (6.0 mg) were dissolved in anhydrous DMSO (1 mL) and stirred under argon atmosphere. Triethylamine (15 μL) was added to the reaction mixture and monitored by LC-MS. After the complete disappearance of nigericin ester, the reaction mixture was purified by RP-HPLC using triethylammonium acetate buffer (10 mM, pH=7). The EC-119-Nigericin ester conjugate was desalted using a mixture of MeOH/$H_2O$ which resulted in the formation of broad peak of the conjugate. Hence the other fractions of RP-HPLC were lyophilized directly to obtain folate nigericin ester conjugate (1) in moderate yield.

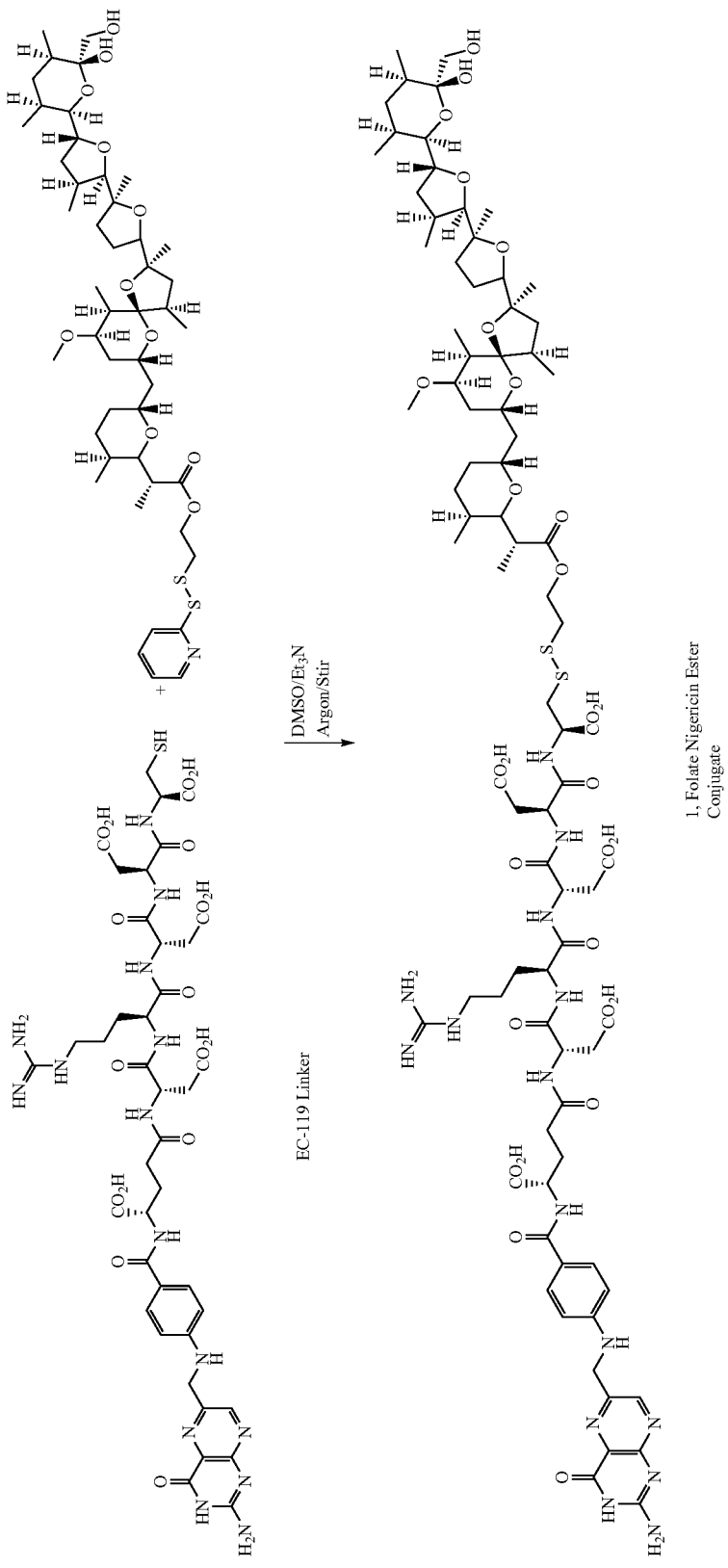

Preparation of Pyridyldisulfide Carbamate of Nigericin (5)

Pyridyldisulfide ethylamine hydrochloride (43 mg) in $CH_2Cl_2$ (1 mL) was neutralized with 1N NaOH (1 mL) and extracted with $CH_2Cl_2$ (3×15 mL). The organic extract was dried over anhyd.$Na_2SO_4$ and filtered. To the filtrate, Proton Sponge (83 mg) was added and cooled to 0° C. Diphosgene (13 µL) was added to the reaction mixture over a period of a minute at 0° C. HPLC analysis showed the formation of the intermediate pyridyldisulfide ethylisocyanate which was utilized without purification in the next step. A portion of the in situ prepared pyridyldisulfide ethylisocyanate (0.2 mL from the above reaction mixture) was added to nigericin free acid (9 mg) in $CH_2Cl_2$ at 0° C. and stirred over weekend under argon. Thin layer chromatography (hexane:ethylacetate:acetic acid, 50:50:1) showed formation of pyridyldisulfide carbamate of nigericin in about 30% which was confirmed by appropriate molecular ion peak by LC-MS analysis. The crude reaction mixture was used for conjugation in next step without further purification.

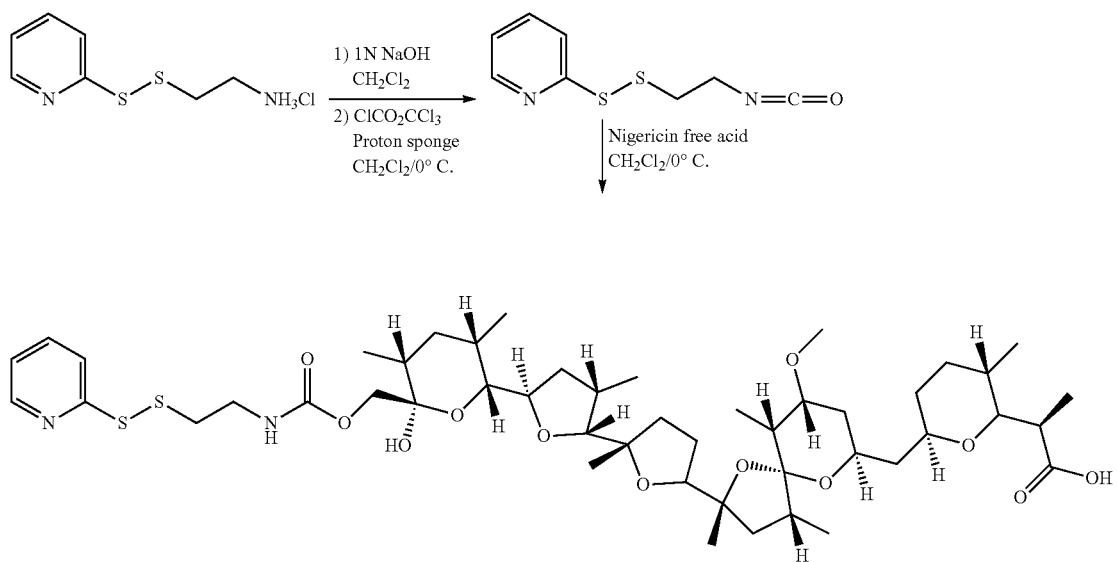

Preparation of Folate-Carbamate Nigericin Conjugate 5

Pyridyldisulfide carbamate of nigericin reaction mixture and EC-119 (20 mg) were dissolved in anhydrous DMSO (1 mL) and stirred under argon atmosphere followed by addition of triethylamine (48 µL). The reaction mixture was monitored by LC-MS and after 2 h, it was purified by RP-HPLC using triethylammonium acetate buffer (10 mM, pH=7, 10-100% MeOH, 30-min run). Folate-carbamate nigericin conjugate was desalted using a mixture of MeOH/$H_2O$ which resulted in the formation of broad peak of the conjugate. Hence the other fractions of RP-HPLC were lyophilized directly to obtain folate-carbamate nigericin conjugate in moderate yield.

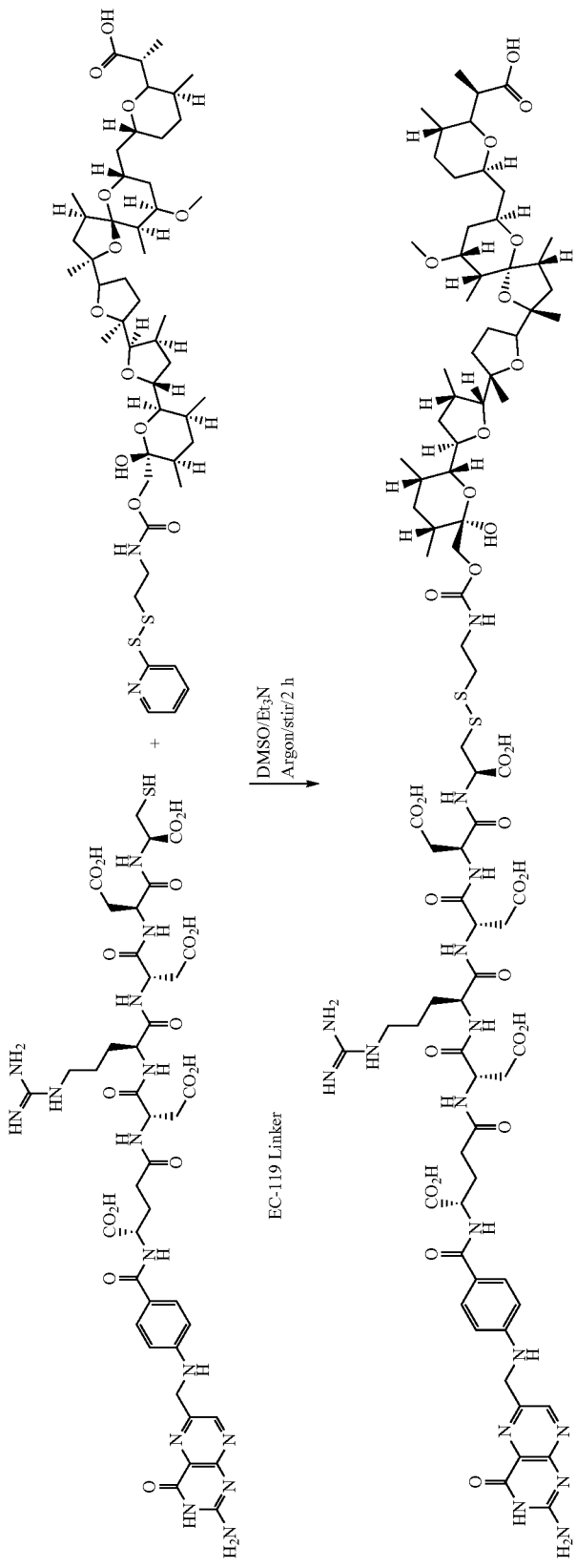

Preparation of Multilamellar Liposomes Containing Calcein Dye 20 mg of egg PC, 8 mg of cholesterol and 2 mg of phosphatidil glycerol (PG) were dissolved in 2 ml of chloroform/methanol solvent mixture (2:1 vol/vol) in a 50-mL round flask by slight warming of the contents (40-50° C.). The solvent was then evaporated on a rotary evaporator under reduced pressure so that a thin film of lipid was deposited on the walls of the flask. The residual solvent was evaporated by connecting the flash to high vacuum for an hour. 1 ml of 0.1 M $Na_2HPO_4$ buffer containing 2% calcein dye was added to the lipid film in the flask and the lipid film was broken by stirring with few magnetic glass beads to give a fluorescent milky suspension of liposomes. The suspension was allowed to stand at room temperature or above the transition temperature of lipids to complete the liposome formation process. The liposomes were purified by passing through a Sephadex column using a mixture of 130 mM NaCl and 5 mM $K_3PO_4$ buffer as eluant.

Preparation of DUPA-S,S-Rhodamine Compound

The DUPA compound is prepared using procedures similar to those described in Examples 8 and 2AA of WO 2009/026177, incorporated herein by reference.

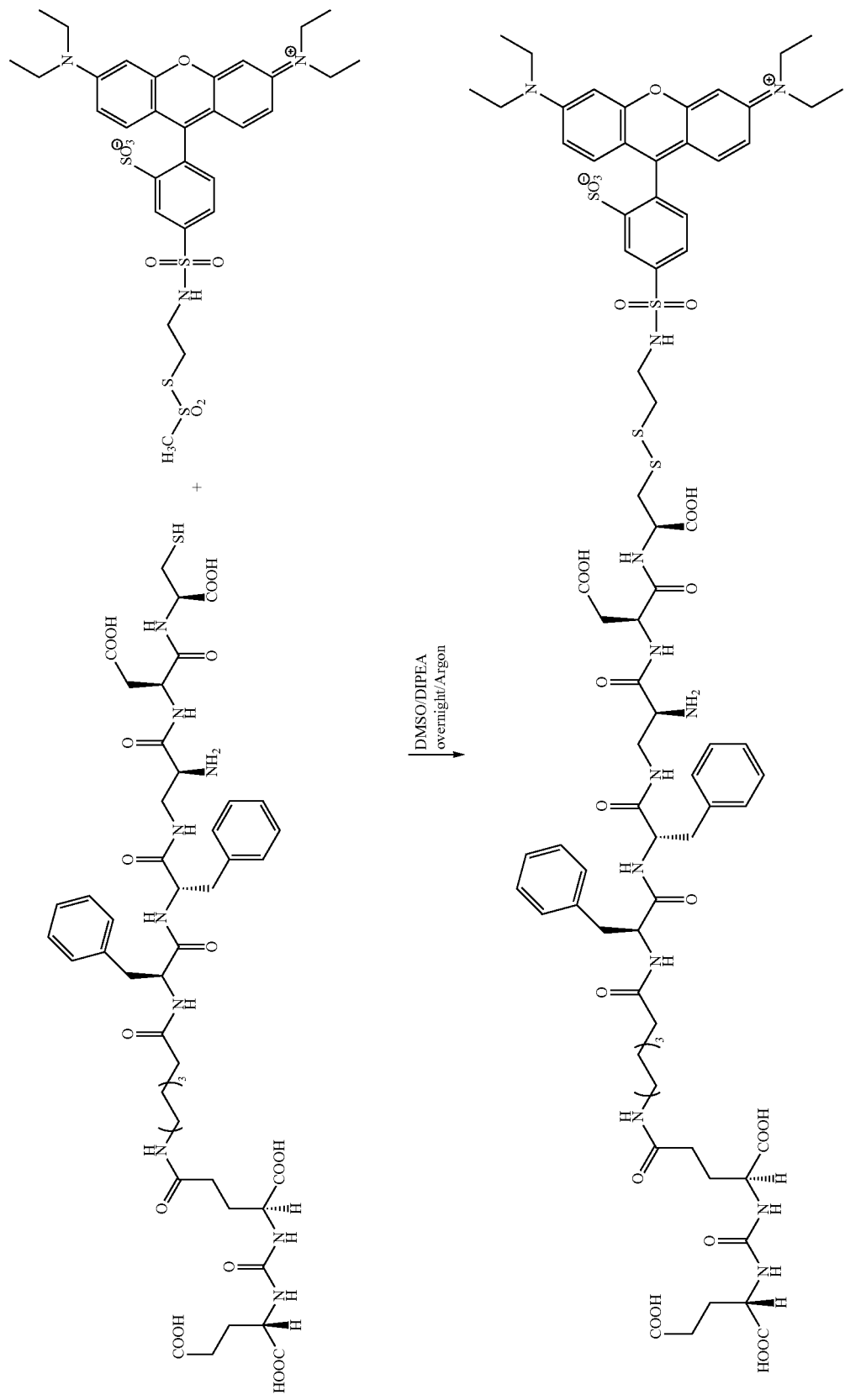

Preparation of DUPA-S-S-Nigericin Conjugate

The conjugate may be prepared using the DUPA linker of Example 8 of WO 2009/026177 and the above described activated nigericin ester as shown below.

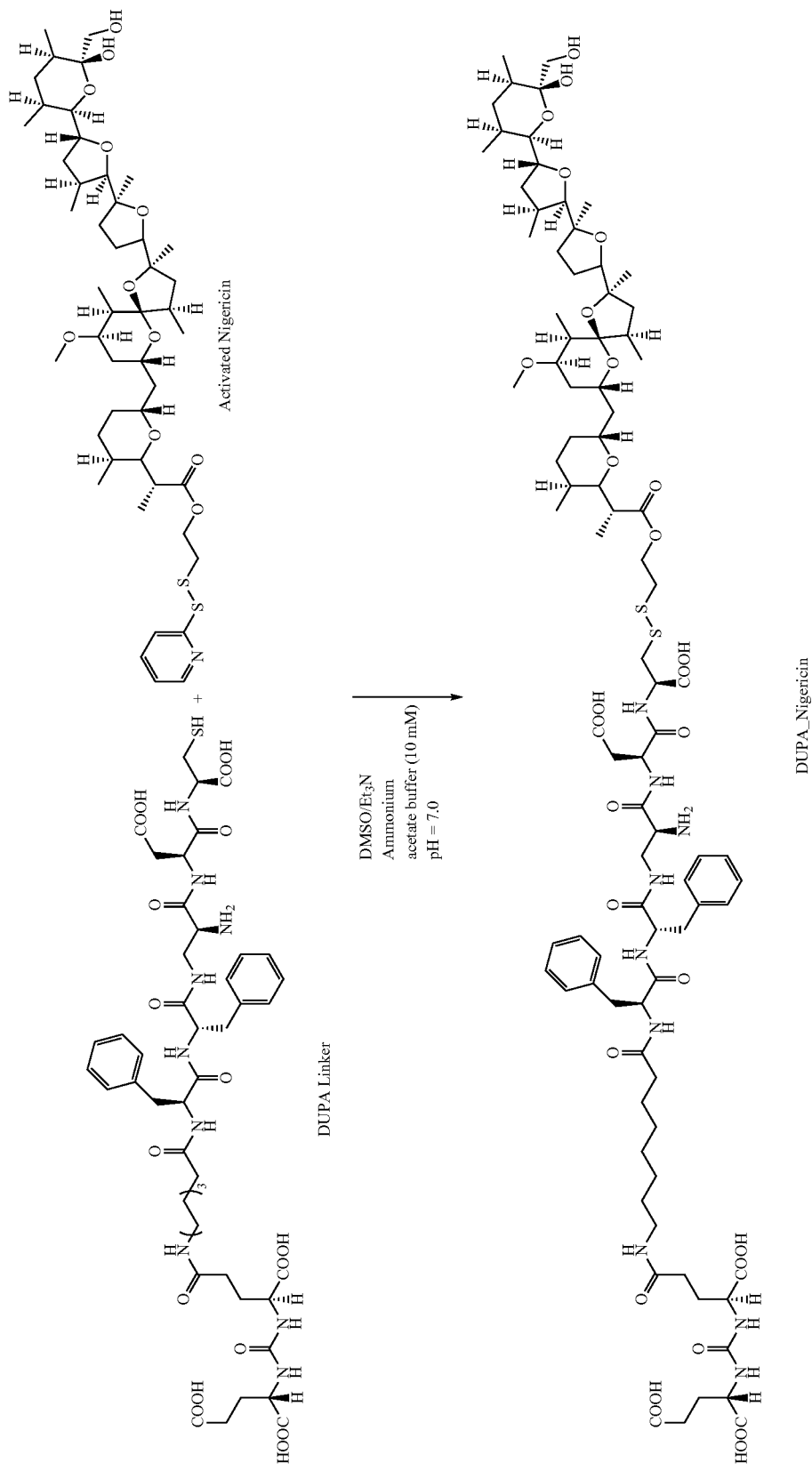

Preparation of Folate-S,S-Nigericin-S-S-Rhodamine Dual Conjugate

The protected folate-S,S-rhodamine compound may be obtained from the thiol intermediate described at Example 9 of WO 2007/022493, incorporated herein by reference, and the activated rhodamine derivative shown above. The compound was deprotected and coupled with the above described activated nigericin ester as shown below to form the dual conjugate.

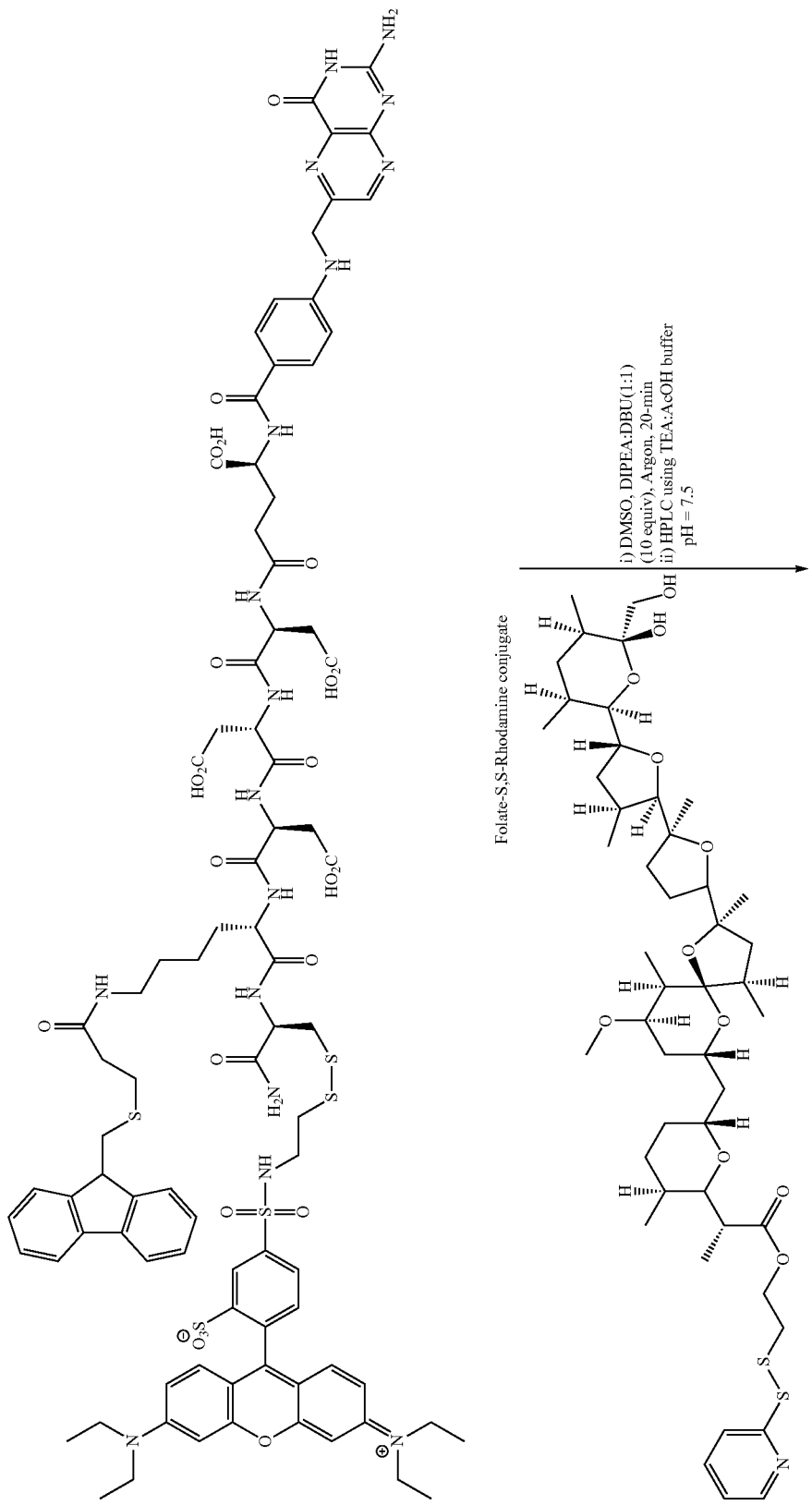

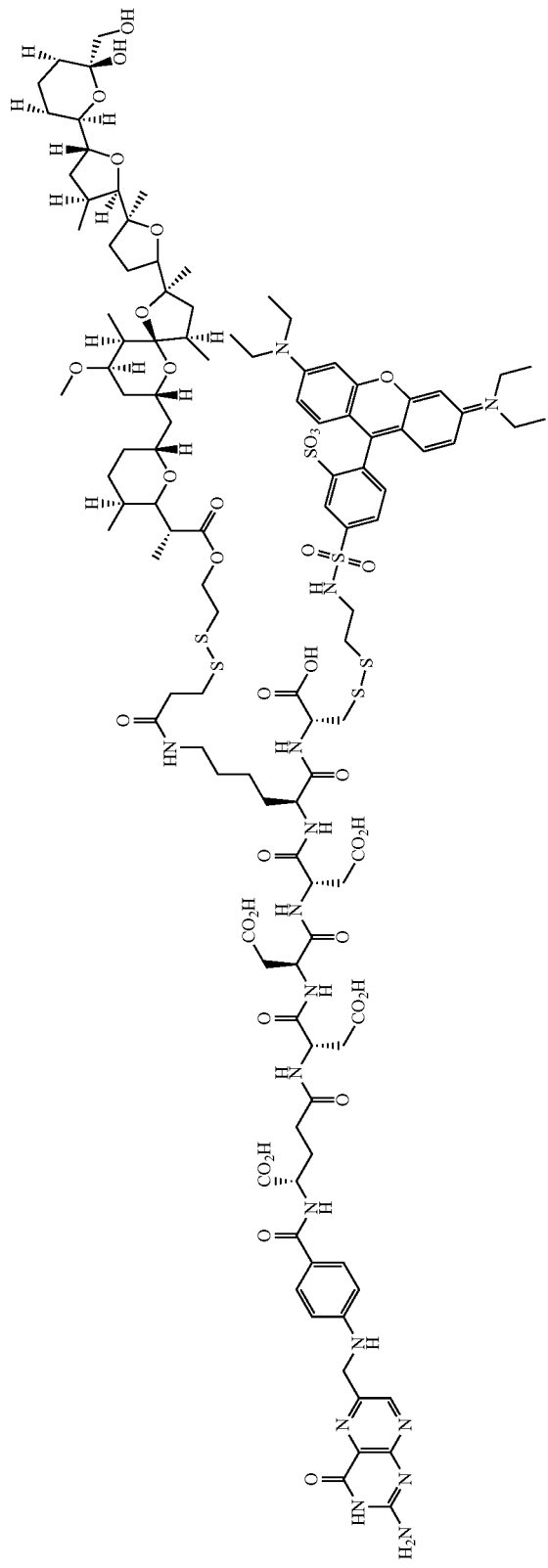
-continued
Folate-S,S-Nigericin-S,S-Rhodamine Conjugate

Preparation of Pyridyldisulfide Carbamate of Salinomycin

A mixture of salinomycin free acid (0.0133 mmol), DCC (0.0266 mmol) and pyrrolidino pyridine (0.0201 mmol) was prepared in anhydrous $CH_2Cl_2$ before adding PyS-S$(CH_2)_2$OH (0.0665 mmol) in $CH_2Cl_2$ (0.3 mL) under argon at room temperature (RT) and stirred for 14 h. The dicyclohexyl urea byproduct precipitated out from the reaction mixture as the reaction proceeded and reaction progress was monitored by LC-MS under the conditions outlined in Table 1. After completion of the reaction, solvent was evaporated from the reaction mixture and the resulting material was dissolved in DMSO and purified by RP-HPLC as outlined in Table 1 (X, =280 nm, binary solvent gradient: 60% to 100% B in 30 min run, solvent A: 20 mM $NH_4OAc$, pH 7.0, solvent B: $CH_3CN$, 26 mL/min). The product pyridyldisulfide ethyl ester of salinomycin was isolated by removing acetonitrile from the fractions before freezing them in liquid $N_2$ and lyophilizing for 48 h. The ethyl ester of salinomycin-pyridyldisulfide was obtained with an 82% yield, as confirmed by LC-MS (product peak at $R_f$=11 min for (M+H)=921.27 where M=molecular mass of the salinomycin ester).

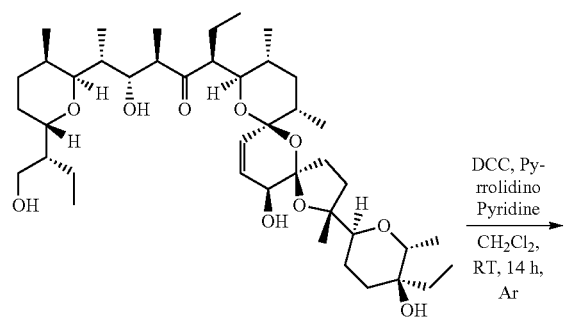

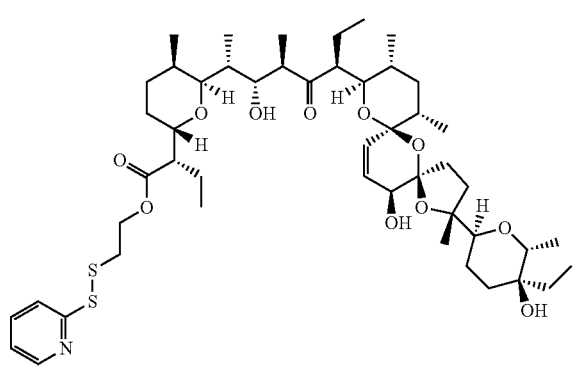

Preparation of Fol_S-S-Rhodamine Conjugate

Synthesis of Fol_Cys linker: Cys(4-methoxytrityl)-Wang resin (150 mg, 0.47 mmol) was swollen with DCM (3 mL) followed by DMF (3 mL) in each 15 min period of time. After swelling the resin in DMF, a solution of Fmoc-Lys (ivDde)-OH (2.5 eq.), PyBOP (2.5 eq.) and DIPEA (2.5 eq.) in DMF was added. Argon was bubbled for 2 h, and resin was washed with DMF (3×3 mL) and i-PrOH (3×3 mL). The coupling efficiency was assessed by the Kaiser test. A solution of 20% piperidine in DMF (3×3 mL) was added to the resin and argon was bubbled for 5 min. The resin was washed with DMF (3×3 mL) and isopropyl alcohol (i-PrOH, 3×3 mL). Formation of free amine was assessed by the Kaiser test. The above sequence was repeated for 5 more coupling steps to couple Fmoc-Asp(O$^t$Bu)-OH, Fmoc-Asp (O$^t$Bu)-OH, Fmoc-Asp(O$^t$Bu)-OH, Fmoc-Glu-OtBu, and $N^{10}$-(Trifluoroacetyl)-Pteroic acid ($N^{10}$-TFA-Ptc). Then, TFA ($CF_3CO$) group in $N^{10}$-pteroate and ivDde protecting group from Fmoc-Lys(ivDde)-OH were deprotected by stirring with 3% hydrazine solution in DMF for 15 min. The resin was washed with DMF, i-PrOH and finally one more coupling reaction with Fluorenylmethylthiopropionic acid under PyBOP/DIPEA conditions was repeated. After completion this coupling reaction, resin was washed with DMF (3×3 mL) followed by i-PrOH (3×3 mL) and dried for 20 min under argon to remove all traces of solvents. Finally, the compound was cleaved from the resin using a trifluoroacetic acid (TFA): triisopropylsilane:ethanedithiol:$H_2O$ cocktail (92.5:2.5:2.5:2.5) and concentrated under vacuum. The concentrated product was precipitated in diethyl ether (3×10 mL) followed by centrifugation, and was dried under vacuum. The crude product was purified using preparative RP-HPLC as shown column conditions in Table 1 [λ=280 nm; solvent gradient: 0% B to 80% B in 30 min run, A=20 mM $NH_4OAC$, pH=5, B=$CH_3CN$, 30 min run]. Acetonitrile was removed from the product fractions using the rotaevaporator under vacuum, followed by freezing, and lyophilization to get Fol_Cys linker solid material which was confirmed by LC-MS, conditions as shown in Table 1 [5-80% B, pH=7.0, 9 min run, product peak at $R_f$=3.8 min] for (M+760)=1284.9.

Synthesis of Fol_S-S_Rhod Conjugate: To a solution of Fol_Cys linker (9.25 mg, 0.0072 mmol, 1.0 eq) and sulpho-rhodamine dye (5.0 mg, 0.0072 mmol, 1.0 eq) in dry DMSO (200 μL) was added excess of N,N-diisopropylethylamine (DIPEA, 25 μL) under argon at RT. The reaction was stirred overnight at RT and purified using preparative RP-HPLC [X, =280 nm; solvent gradient: 0% B to 80% B in 30 min run, A=20 mM $NH_4OAc$, pH=7, B=$CH_3CN$]. Acetonitrile was removed from the product fractions using the rotaevaporator under vacuum, followed by freezing, and lyophilization, to get Fol_S-S_Rhod compound which was confirmed by LC-MS, conditions as shown in Table 1 [0-80% B, pH=7.0, 9 min run, product mass (M+H)=1901.13].

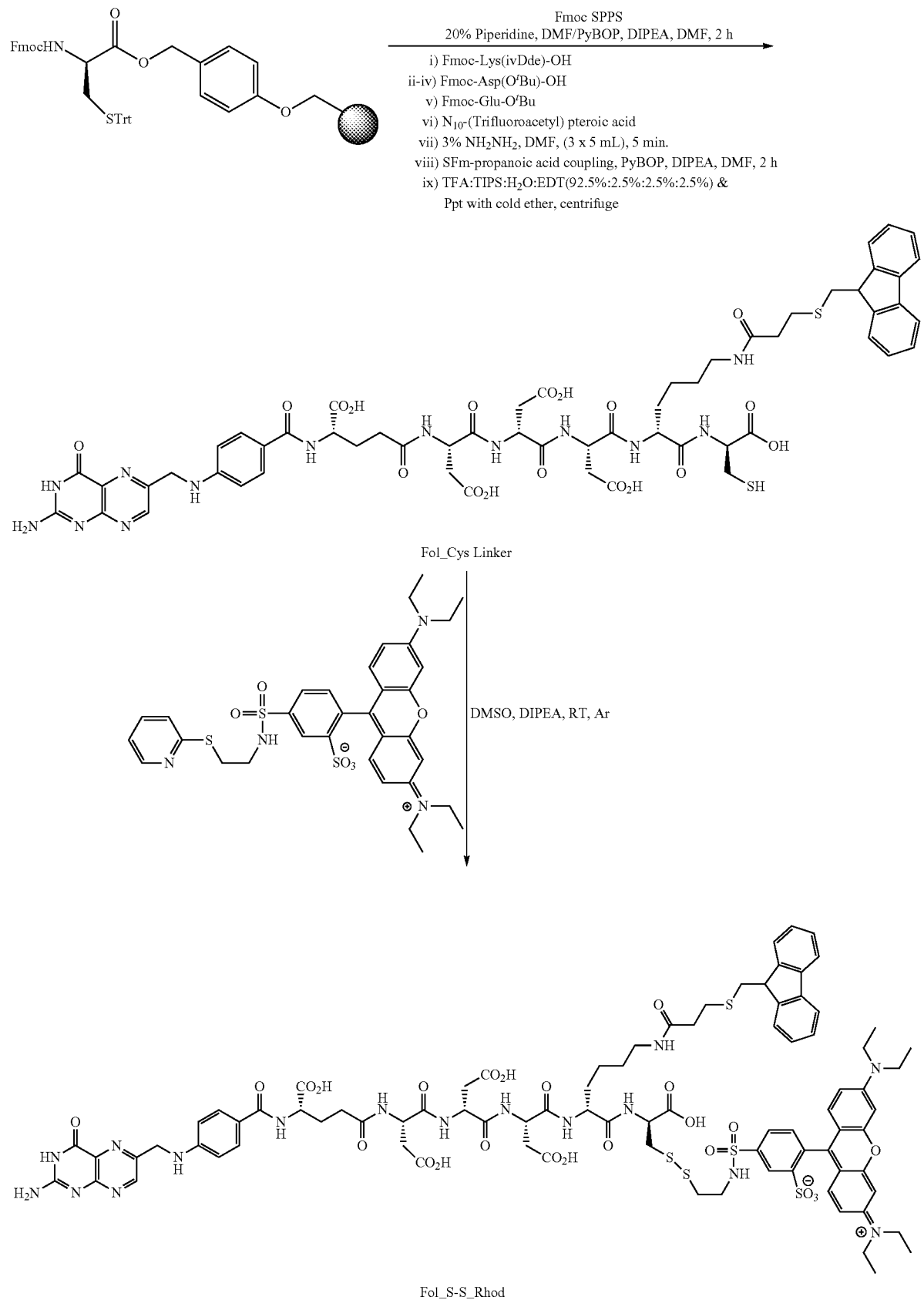

Preparation of Folate-Salinomycin-S-S-Rhodamine Conjugate

Pyridyldisulfide ethyl ester of salinomycin (5.76 mg, 0.00626 mmol) and Fol_S-S_Rhod (10.8 mg, 0.0057) were dissolved in anhydrous DMSO (0.5 mL) and stirred under argon atmosphere. The mixture of DBU:DIPEA (1:1, 19 μL in 100 μL DMF) was added to the reaction mixture at RT and monitored by LC-MS, conditions as shown in Table 1. After the complete disappearance of salinomycin ester, the reaction mixture was purified by RP-HPLC [λ=280 nm; solvent gradient: 0% B to 100% B in 30 min run, A=20 mM $NH_4OAc$, pH=7, B=$CH_3CN$] and the Fol_S-S_Rhod S-S Salinomycin ester conjugate was isolated. The acetonitrile was removed from product fractions using the rotoevaporator under vacuum, followed by freezing, lyophilization and product isolation in moderate yield, as confirmed by LC-MS.

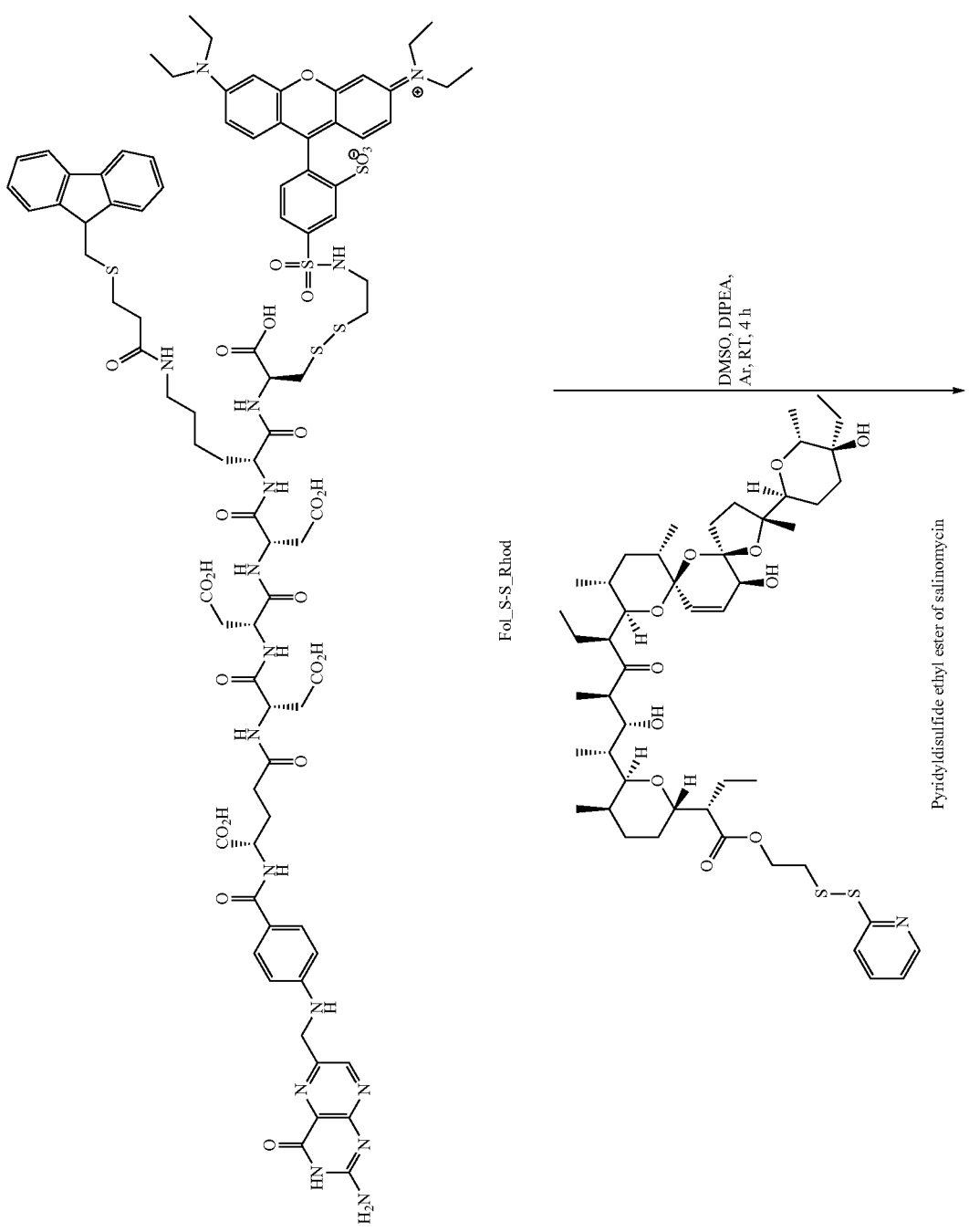

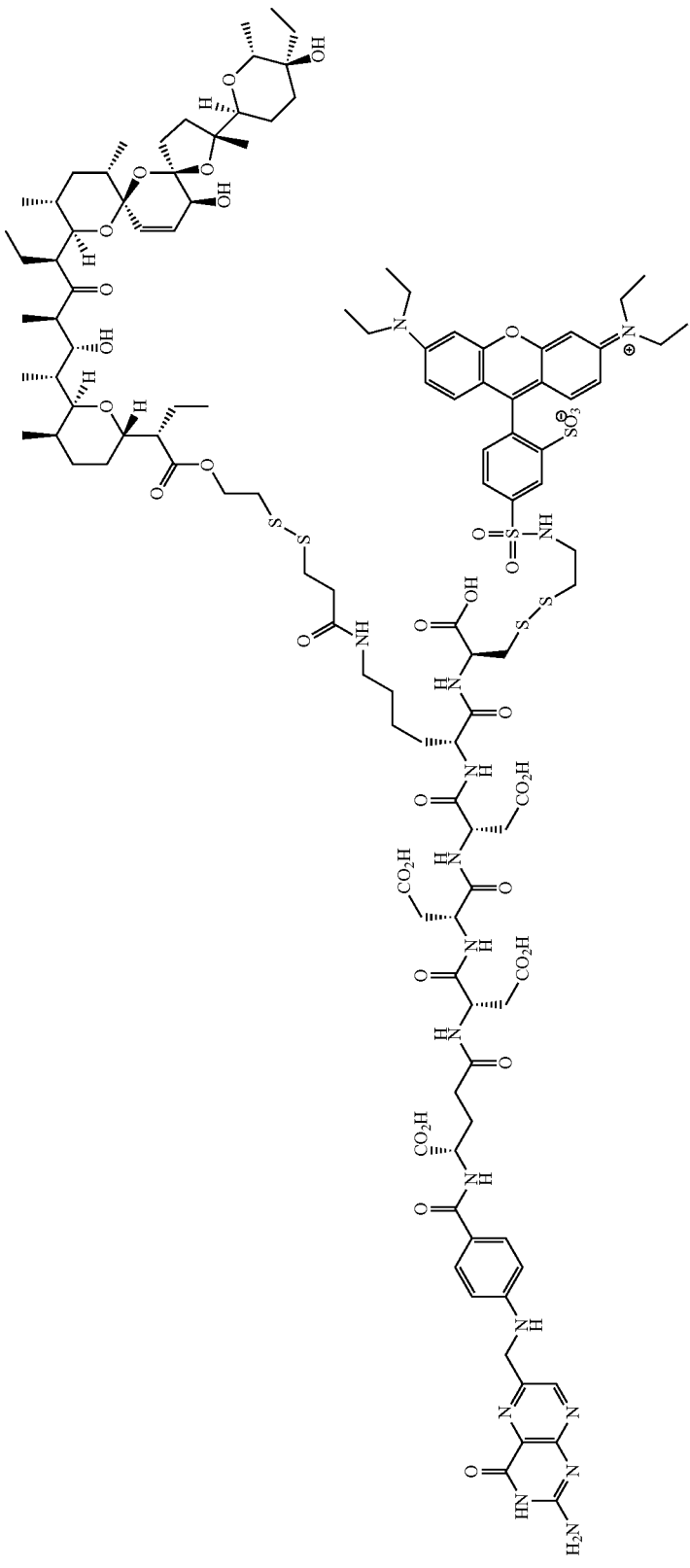
Fol_S-S_Salinomycin_S-S_Rhod Conjugate

TABLE 1

Abbreviations and Source Information

| Term | Description | Source |
|---|---|---|
| Calcein | Calcein dye | Life Technologies, Div. of Fisher Scientific, Pittsburgh, PA |
| | $CHCl_3$ | EMD Millipore, Billerica, MA |
| | $CH_2Cl_2$ (anhydrous) | Sigma-Aldrich, St. Louis, MO |
| | $CH_3COOH$ | Sigma-Aldrich, St. Louis, MO |
| | Diphosgene | Acros Organics, distributed by Fisher Scientific, Pittsburgh, PA |
| DMSO | Dimethyl sulfoxide | Sigma-Aldrich, St. Louis, MO |
| EC-119 | (2R,5S,8S,11S,14S,19S)-19-(4-(((2-amino-4-oxo-3,4-dihydropteridin-6-yl)methyl)amino)benzamido)-5,8,14-tris(carboxymethyl)-11-(3-guanidinopropyl)-2-(mercaptomethyl)-4,7,10,13,16-pentaoxo-3,6,9,12,15-pentaazaicosane-1,20-dioicacid | Endocyte, Inc., West Lafayette, IN |
| | $HClO_4$ | Sigma-Aldrich, St. Louis, MO |
| DCC | N,N'-Dicyclohexylcarbodiimide | Alfa Aesar, Ward Hill, MA |
| EtOAc | Ethyl Acetate | Sigma-Aldrich, St. Louis, MO |
| FDRPMI | Folate-Deficient RPMI (Roswell Park Memorial Institute) Medium | Sigma-Aldrich, St. Louis, MO |
| FR | Folate Receptor | |
| | $HClO_4$ | Sigma-Aldrich, St. Louis, MO |
| LC-MS | Liquid Chromatography-Mass Spectrometry | Performed on a Waters LC-MS system (Milford, MA) with a Waters Micromass ZQ mass spectrometer; Xbridge ™ Shield RP-18, 5 µm, 3.0 × 50 mm column; flow rate of 0.75 mL/min; mobile phase of 20 mM $NH_4HCO_3$ buffer, pH 7. |
| MeOH | Methanol | Sigma-Aldrich, St. Louis, MO |
| | $Na_2SO_4$ | Mallinckrodt-Baker, Phillipsburg, NJ |
| | Nigericin, sodium salt | A.G. Scientific, San Diego, CA |
| Proton Sponge ® | Registered trademark for N,N,N',N'-tetramethyl-1,8-naphthalenediamine | Sigma-Aldrich, St. Louis, MO |
| $PyS-S(CH_2)_2OH$ | 2-(2-pyridyldithio)-ethanol | Endocyte, Inc., West Lafayette, IN |
| | Pyridyldisulfide ethylamine HCl | Molecular Biosciences, Boulder, CO |
| | Pyrrolidinopyridine | Sigma-Aldrich, St. Louis, MO |
| RP-HPLC | Reversed-Phase High-Performance Liquid Chromatography | Performed on a Waters RP-HPLC system (Milford, MA); XTerra ® Prep MS C18 OBD ™ 50 µm, 19 × 30 mm column; binary gradient elution with 10 mM triethylammonium acetate buffer, pH 7 and methanol; flow rate 26 mL/min; UV detection 280 nm |
| RT | Room Temperature | |
| TLC | Thin-Layer Chromatography: Silica Gel 60 F254 | EMD Millipore, Billerica, MA |
| | Triethylamine | Sigma-Aldrich, St. Louis, MO |
| | Triethylammonium acetate | Sigma-Aldrich, St. Louis, MO |

Method Examples

Endosomal Release Using Multilamellar Liposomes (LMV) Encapsulating 2% Calcein Dye. In one illustrative example, a model for endosomal release is demonstrated using multilamellar liposomes (LMV) encapsulating 2% calcein dye together with a $Na^+$ containing buffer, as described above. Liposomes can be prepared to resemble endosomal compartments of cells, which have $Na^+$ as the major intra-endosomal cation and $K^+$ as the major extra-endosomal (cytosolic) cation. This distribution of high $Na^+$ inside the liposome with high $K^+$ outside the liposome is similar to the distribution of high $Na^+$ inside the endosome with high $K^+$ outside the endosome following receptor-mediated endocytosis into a living cell. Liposomes resemble endosomal compartments of cells and are considered to be a useful model for a live cell plasma membrane. Multilamellar liposomes, encapsulated with calcein dye dissolved in buffer, were synthesized by a method described in the literature and were purified by Sephadex chromatography using a mixture of 130 mM NaCl and 5 mM $K_3PO_4$ buffer as an eluant to remove free dye and broken liposome vesicles. In an illustrative example, the addition of nigericin or a folate-nigericin ester conjugate 1 (10 nM) to a liposome encapsulating a dye resulted in a lower release (20% to 25%) of the calcein dye (relative to Triton X 1.5 which is used as a control for 100% release; see FIG. 1A).

In another illustrative example, an increase in the intensity of the signal for the calcein dye was observed when the concentration of the added nigericin or nigericin conjugate was increased by a factor of ten (FIG. 1A), resulting in release of 68% to 72%% of the dye. The dye release was confirmed by running a positive control using Triton X 1.5, and a negative control using buffer and DMSO, where no absorption occurred without addition of nigericin or nigericin-conjugate as shown in FIG. 1A. This indicates that the release of dye from liposomes is caused by the added ionophores that translocate K+ into the liposome without transporting sodium out of the liposome, thereby leading to the osmotic swelling of the liposome (and not by residual solvent or impurities).

Figure 1B:
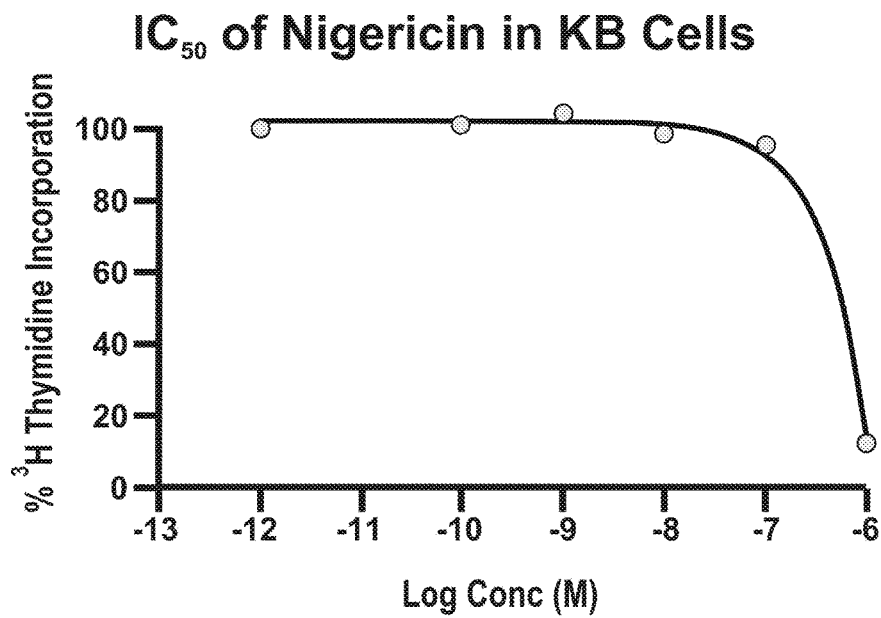
FIG. 1B shows the results of a cytotoxicity study of nigericin in KB cells demonstrating that the endosomal escape-facilitating molecule nigericin is not toxic to the cells at those concentrations at which it is employed for enhancing endosomal escape.

Cytotoxicity Study of Nigericin in KB Cells After the demonstration of a successful release of entrapped dye from liposomes by nigericin or nigericin ester, a study in KB cells, a human cancer cell line derived from a cancer of the nasopharynx and which over expresses folate receptors, was carried out. As shown in FIG. 1B, a study of the effects of nigericin on the growth of KB cells identified an $IC_{50}$ concentration of 12 μM and demonstrated that the endosomal escape facilitating molecule nigericin is not toxic to the cells at concentrations at which it is employed for enhancing endosomal escape.

Figure 2:
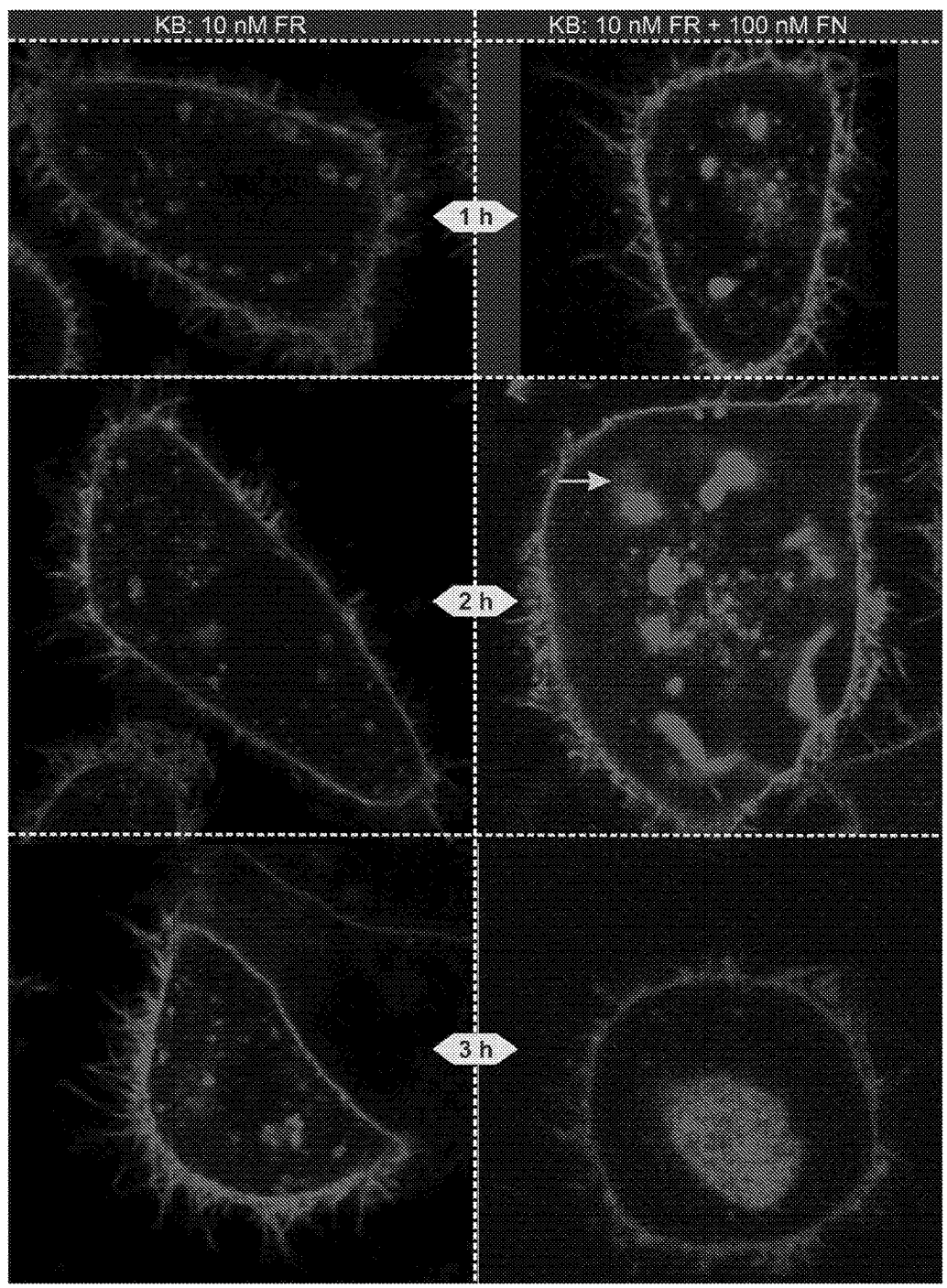
FIG. 2 shows the hourly status of KB cells after treatment with 10 nM folate-rhodamine conjugate or the combination of 10 nM folate-rhodamine conjugate plus 100 nM folate nigericin ester conjugate. The arrow indicates one example of pluming associated with the escape of dye from an endosome.

Effect of Folate Nigericin Ester Conjugate 1 on Release of Rhodamine Dye in KB Cells. In another illustrative example, KB cells (a human cancer cell line derived from a cancer of the nasopharynx that expresses folate receptors) grown on chambered borosilicate glass dishes were co-incubated with folate nigericin ester conjugate 1 and folate-S,S-rhodamine conjugate 2 affinity of the folate-nigericin ester conjugate was found to be 5 times lower than the binding affinity of the folate-rhodamine compound. Without being bound by theory, it is believed that using concentration ratios of 1 to 2 in multiples of five ensures that most endosomes contain both the conjugate and the compound. In illustrative examples a mixture of 1 and 2 at concentration ratios of 5:1, 10:1 and 15:1 were incubated with the KB cells. It was found that a concentration ratio of 10:1 between 1 and 2 showed considerable release of rhodamine dye from the endosome. Endosomal release of the rhodamine dye using other concentration ratios was lower. The cells were monitored for several hours under confocal microscopy for release of dye from the endosomes. It was found that high release of dye occurs between 1-3 hours as shown in separate panels of FIG. 2. The control cells on the left side of each image were incubated with the folate-rhodamine compound in the absence of folate nigericin ester conjugate 1. Without being bound by theory, it is believed that the nigericin-mediated transport of K+ into the endosomes causes endosome swelling and bursting, as seen in some of the panels around 3 h.

Effect of Folate Nigericin Ester Conjugate 1 on Release of Nucleotides in KB Cells. In another embodiment, release of larger molecules such as siRNA and DNA that are trapped in endosomes is described.

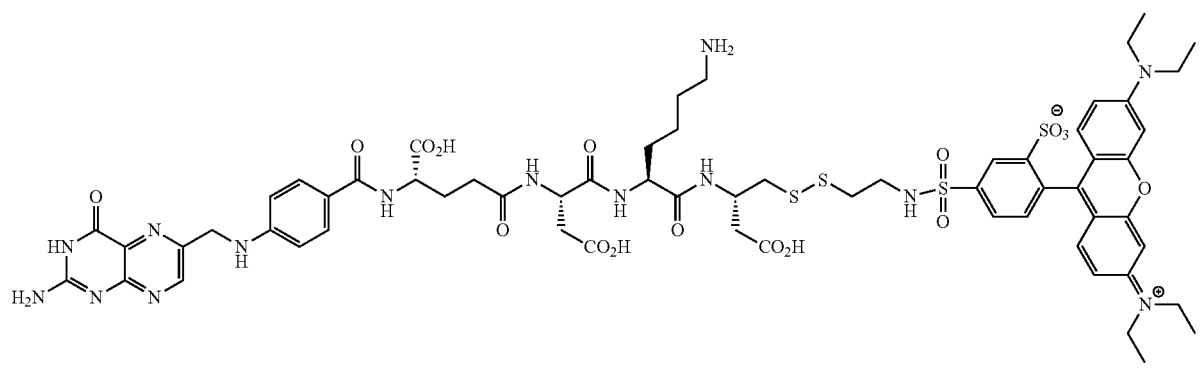

Folate-S-S-Rhodamine
Compound 2 for an hour to accumulate a large number of endosomes inside the cell. The unbound conjugate 1 and compound 2 were washed off with fresh cell culture medium and the cells were then incubated with fresh medium to measure endosomal release of the dye. The endosomes were visualized by the excitation of the rhodamine dye using confocal laser microscopy. In one aspect the co-incubation ratio of 1 and 2 was determined based on the binding affinity constants of conjugate 1 and compound 2 to folate receptors. The binding A. In an illustrative example, release of a DyLight 647 labeled, methylated folate-siRNA compound 3 (which may be prepared in a manner similar to one described in WO 2010/045584) targeted to endosomes of KB cells, using folate nigericin ester 1 is shown. A concentration ratio of 1:2 between 1 and 3 was based on their binding constants to folate receptors in KB cells. An effective concentration for co-incubation was found to be 400 nM and 200 nM for 3 and 1, respectively.

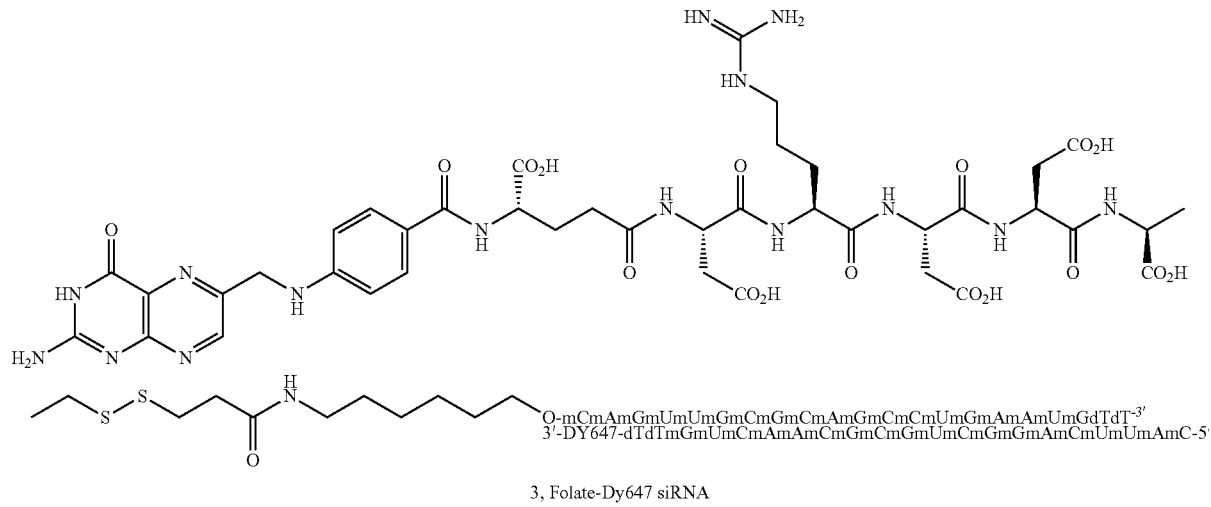

3, Folate-Dy647 siRNA

Figure 3:
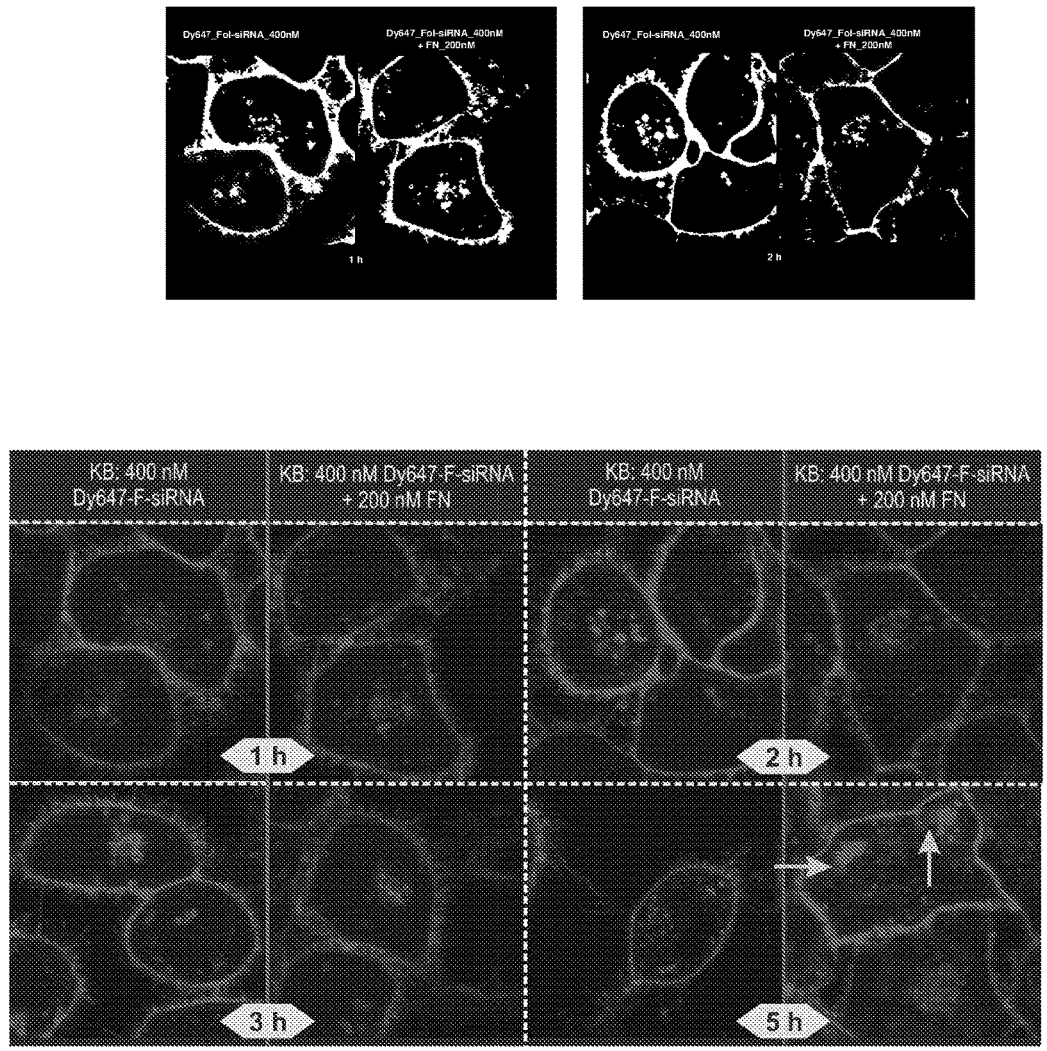
FIG. 3 shows the disposition of a larger molecule: the Dy647-labeled, folate-siRNA conjugate (400 nM) within endosomes of KB cells with or without further treatment by 200 nM of the folate nigericin ester conjugate. As in FIG. 2, the arrow indicates dye release.

B. In another illustrative example the release of DyLight 647 labeled siRNA was monitored by confocal microscopy for several hours (1-6 h) after a brief co-incubation time (1 h) of KB cells with 1 and 3. During the first 3 h of incubation, there was little noticeable release of the fluorescent moiety of DyLight 647 siRNA. During the 5th and 6th hours of incubation, the release of the fluorescent moiety of DyLight 647 took place which was visualized by the formation of large endosomes and cloudy dispersions of the fluorescent moiety of DyLight 647 siRNA in the cytoplasm as seen in the panel diagrams (FIG. 3).

C. In another illustrative example, endosomal release was examined with a Cy5-labeled oligonucleotide molecule 4. The modified oligonucleotide of the example acts as a surrogate for siRNA. Folate-Cy5 labeled 21-mer oligonucleotide 4 was synthesized according to standard procedures and employed to demonstrate endosomal release in KB cells using folate nigericin ester conjugate 1.

Figure 4:
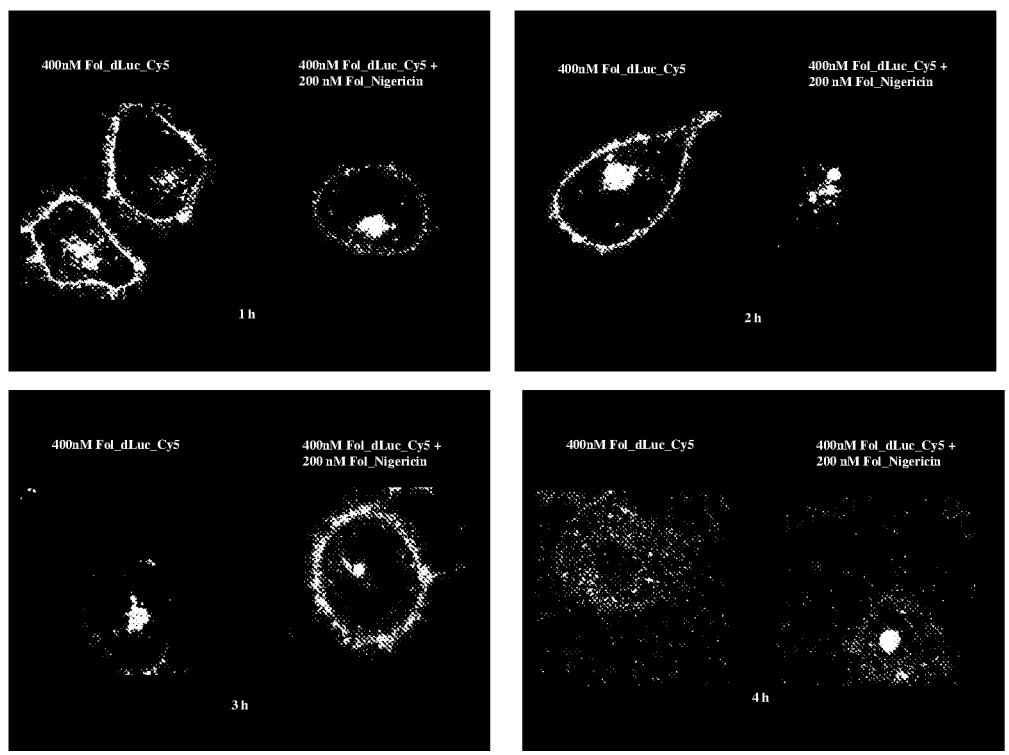
FIG. 4 shows endosomal release of fluorescence derived from folate-Cy5 labeled 21-mer oligonucleotide (400 nM) trapped in endosomes of KB Cells without and with folate nigericin ester (200 nM) at various time intervals.

The swelling of smaller endosomes and release of a Cy5 dye labeled oligonucleotide occurred between 2-4 h as shown in panel diagrams (FIG. 4). Without being bound by theory, it is believed that because Cy5 is a highly photobleachable dye under the conditions of the experiment, the intensity of released dye fades out quickly and the released dye was not as visually prominent compared to rhodamine and DyLight 647 (FIG. 4).

Effect of Folate Nigericin Ester Conjugate 5 on Release of Rhodamine Dye in KB Cells. In another illustrative example, nigericin is conjugated via a carbamate linkage to the primary hydroxyl group. Folate-carbamate nigericin conjugate 5 was synthesized and used to facilitate endosomal release. In this conjugate the primary hydroxyl group of nigericin is conjugated to a folate ligand via a disulfide bridge through the amino group of 2-amino-ethanethiol.

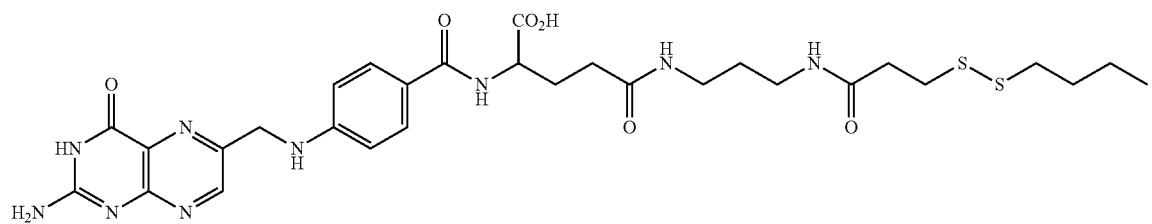

4, Folate-Cy5 DNA

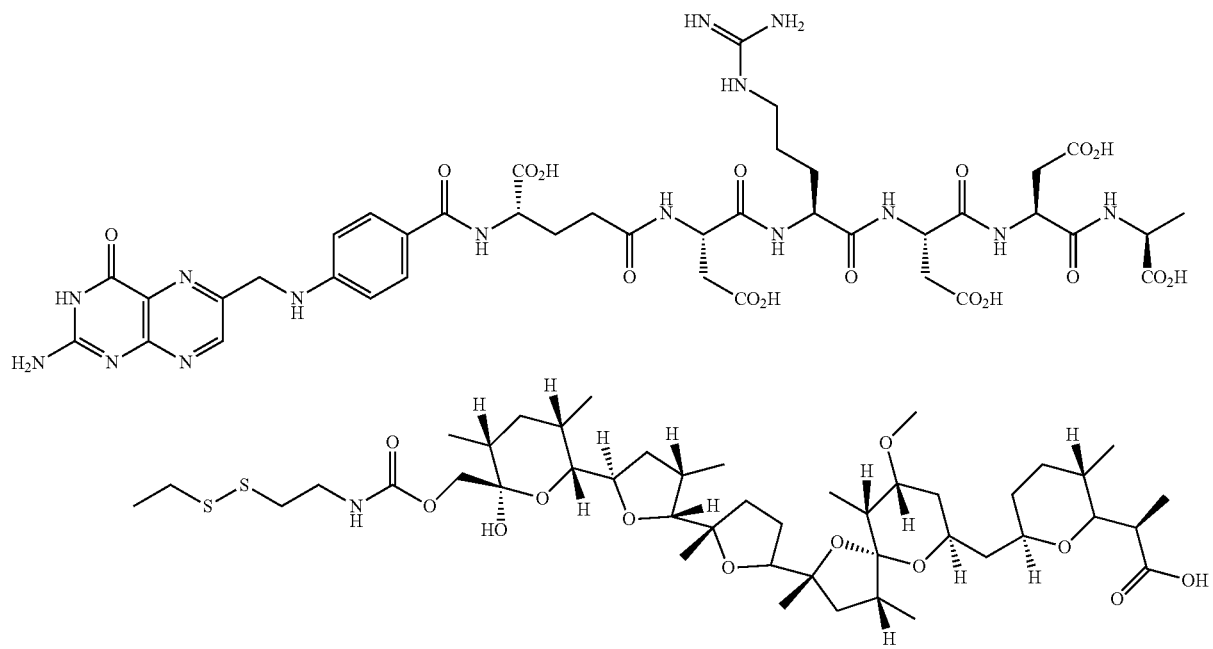

Figure 5:
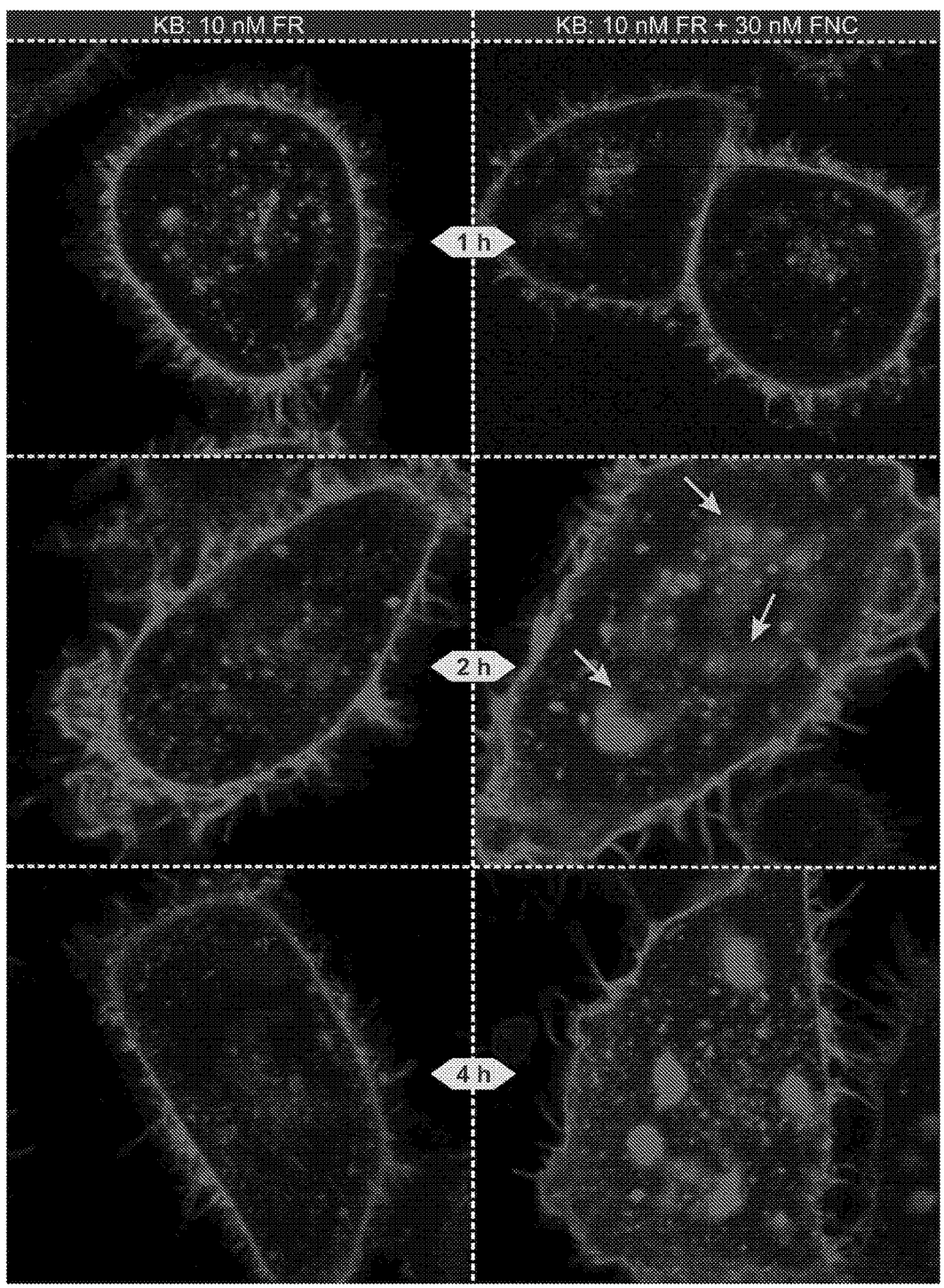
FIG. 5 shows endosomal rhodamine fluorescence using folate rhodamine conjugate (10 nM) without and with folate nigericin carbamate conjugate (30 nM) at various time intervals in KB cells.
Figure 6:
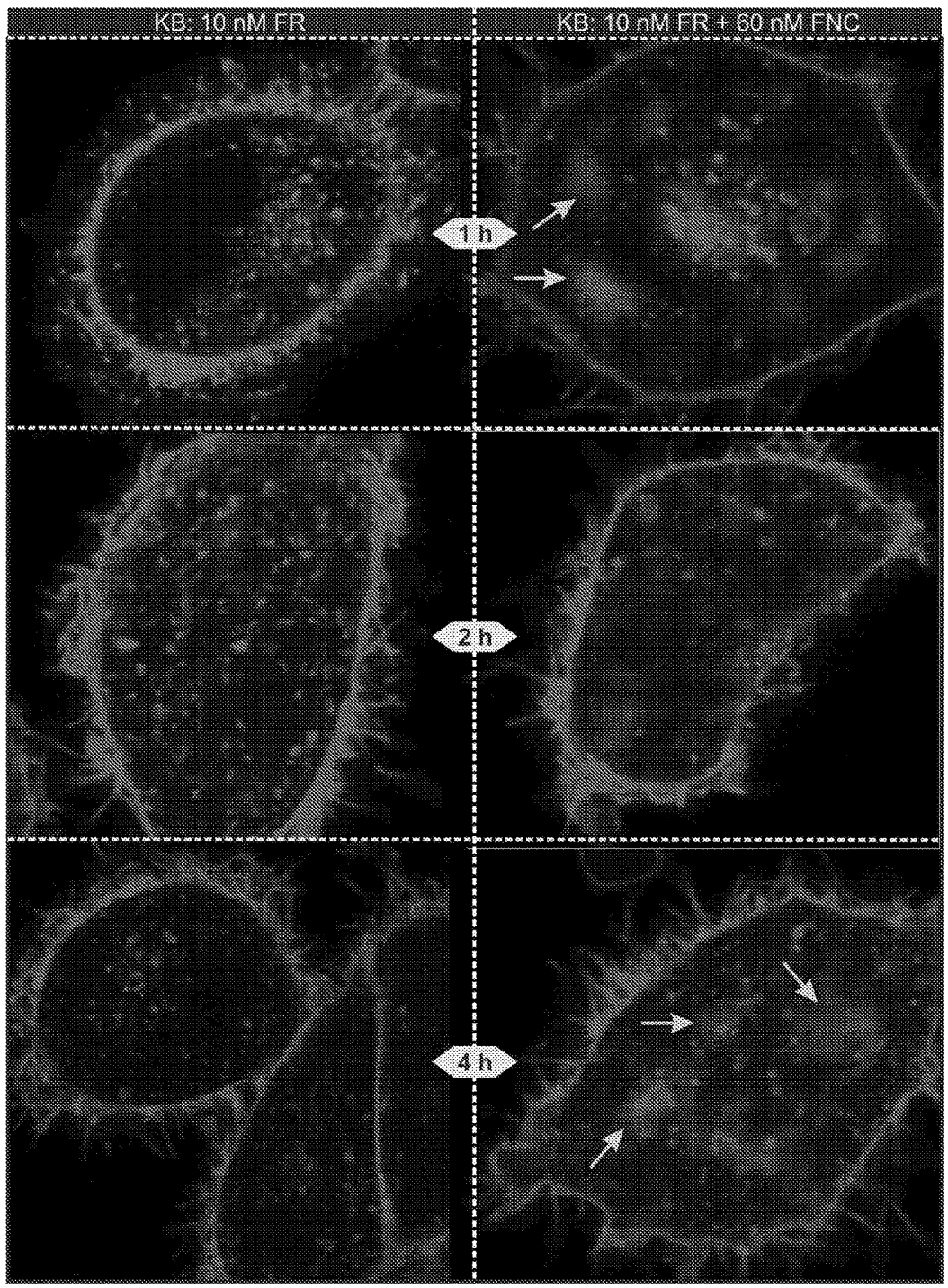
FIG. 6 shows endosomal rhodamine fluorescence using folate rhodamine conjugate (10 nM) without and with folate nigericin carbamate conjugate (60 nM) at various time intervals in KB cells.

The binding affinity constant of the folate carbamate nigericin conjugate 5 to the folate receptor was found to be three times lower compared to folate rhodamine 2 compound. Therefore the concentration ratio of conjugate 5 to compound 2 in multiples of three were used to facilitate formation of endosomes containing both the conjugate and the compound. In another illustrative example, confocal microscopy visualization of KB cells was carried out with a mixture of 5 and 2 at various concentration ratios of 3:1, 6:1 and 9:1, e.g. 30, 60 and 90 nM of the folate carbamate nigericin conjugate 5 with 10 nM folate rhodamine compound 2. Using a 30 nM concentration of carbamate nigericin 5, endosomal release of a rhodamine fluorescent moiety was observed between 2-4 hour (FIG. 5), whereas use of a 60 nM concentration of the carbamate nigericin conjugate 5 caused endosomal release of a rhodamine fluorescent moiety within an hour of co-incubation and the release continued to 4 h as shown in panels of FIG. 6.

Figure 7:
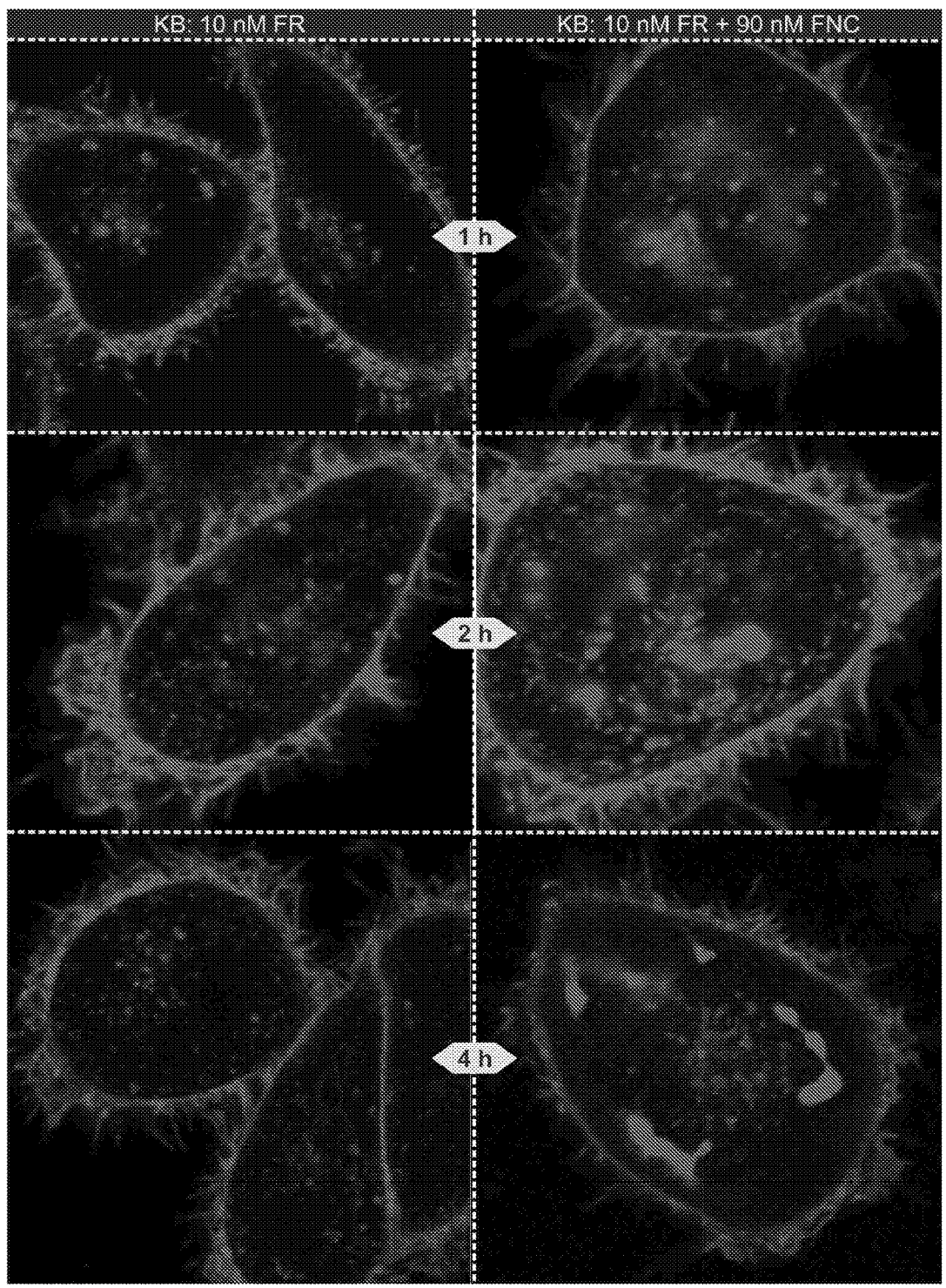
FIG. 7 shows endosomal rhodamine fluorescence using folate rhodamine conjugate (10 nM) without and with folate carbamate nigericin conjugate (90 nM) at various time intervals in KB cells.

Endosomal release of a rhodamine fluorescent moiety was also observed for 90 nM carbamate nigericin conjugate in KB cells from 1-4 hour as shown in the panels of FIG. 7. The effect appears to be similar to the effect of 60 nM carbamate nigericin concentration.

Calcein Release Assay of Liposomes. Purified liposomes were collected from a Sephadex column chromatography and stored in the refrigerator (0-4° C.) before the assay. 10 μL of liposome suspended in 1 mL of buffer was placed in a transparent cuvette and 10 nM or 100 nM of nigericin free acid or folate nigericin was added to the cuvette and the intensity of absorption maximum was measured using fluorescence spectrophotometer. A plot of fluorescent absorbance (AU) was drawn to compare the calcein dye release resulting from the various treatments.

Confocal Microscopy for Endosomal Release. KB cells (100,000 cells/well in 0.5 mL medium) were seeded into thin glass borosilicate labtek chambered dishes and cells were allowed to form a monolayer overnight. Spent medium was replaced with fresh medium (0.5 mL) containing either folate nigericin ester conjugate 1 (100 nM) and folate rhodamine 2 (10 nM) or 1 (200 nM) and Dy647 labeled methylated folate-siRNA 3 (400 nM) or 1 (200 nM) and folate-Cy5 labeled 21-mer oligonucleotide 4 (400 nM) or folate carbamate nigericin conjugate 5 (30, 60 or 90 nM) and folate rhodamine 2 (10 nM) and cells were incubated for 1 h at 37° C. After rinsing with fresh medium (3×0.5 mL), confocal images were acquired using a confocal microscopy (FV 1000, Olympus) over a period several hours (1-6 h) by excitation of at the appropriate frequency for a rhodamine or a DyLight 647 or a Cy5 dye.

Cell Lines and Culture. The folate receptor positive KB cell line was originally derived from a human oral epidermal carcinoma. KB cells used in this study had been maintained by the Cancer Cell Culture Facility in the Purdue University Department of Chemistry. It should be noted that KB cells purchased from the American Type Culture Collection are described as having the same origin but with the subsequent finding, based on isoenzyme analysis, HeLa marker chromosomes, and DNA fingerprinting, that they were actually established via HeLa cell contamination. The cells were cultured in folate-deficient RPMI 1640 medium (Invitrogen, Grand Island, N.Y.) supplemented with 10% heat inactivated fetal bovine serum (Sigma Aldrich, St. Louis, Mo.), penicillin (50 units/mL) and streptomycin (50 μg/mL) 243 and passaged continuously in a monolayer at 37° C. in a humidified atmosphere containing 5% $CO_2$.

Affinity Determination. In order to establish whether a folate-linked ionophore could promote endosomal release in vitro, we prepared folate-nigericin conjugate 2 by esterification of the free carboxylic acid of nigericin. The conjugate also included a self-immolative disulfide linker. As an indicator of endosomal swelling or release, we also prepared a fluorescent folate-rhodamine dye compound 3, also linked via a disulfide linker.

Figure 8:
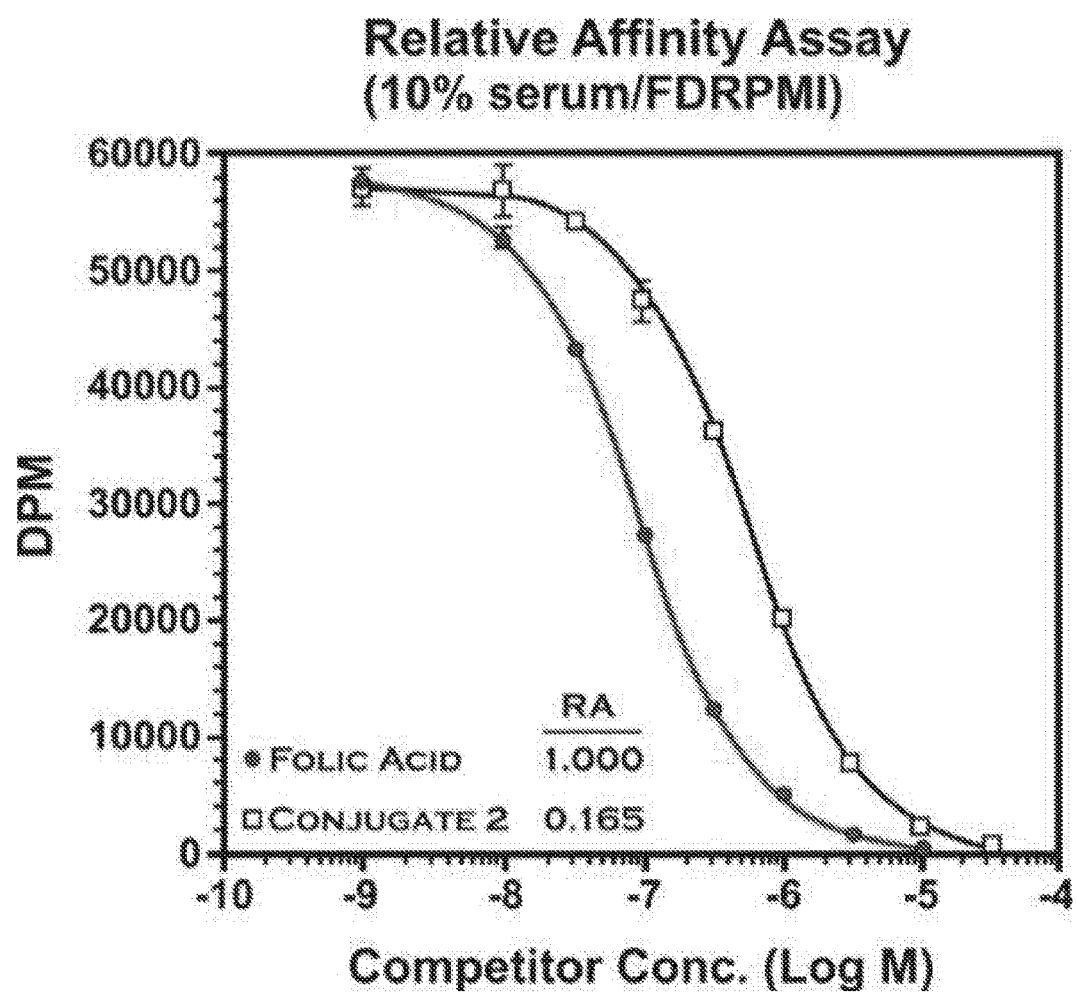
FIG. 8 shows the relative affinity of folic acid versus the folate-nigericin conjugate.

KB cells were selected to assess the folate-nigericin ester conjugate 2 because this cancer derived cell line is associated with high expression of the folate receptor. To ensure that the internalization of the folate-conjugate into the cells would be folate-mediated, a binding assay was performed to determine the relative affinity of the folate-nigericin conjugate compared to folic acid in KB cells. As illustrated in FIG. 8, the relative affinity of conjugate 2 was 0.165.

Figure 9:
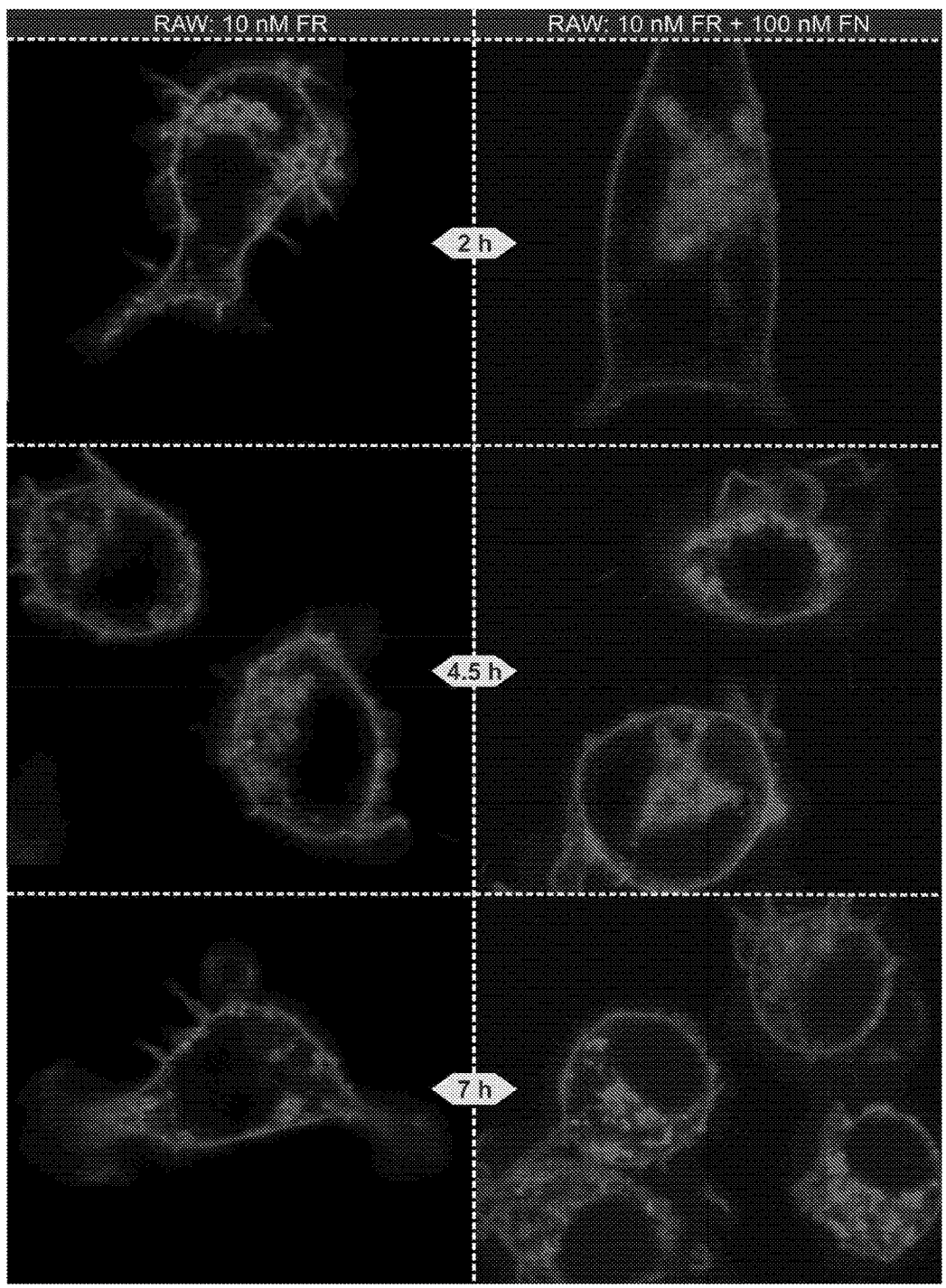
FIG. 9 shows escape of 10 nM FR (folate rhodamine compound) from endosomes in RAW cells as compared with RAW cells treated with both 10 nM FR and 100 nM FN (folate-nigericin conjugate).
Figure 10:
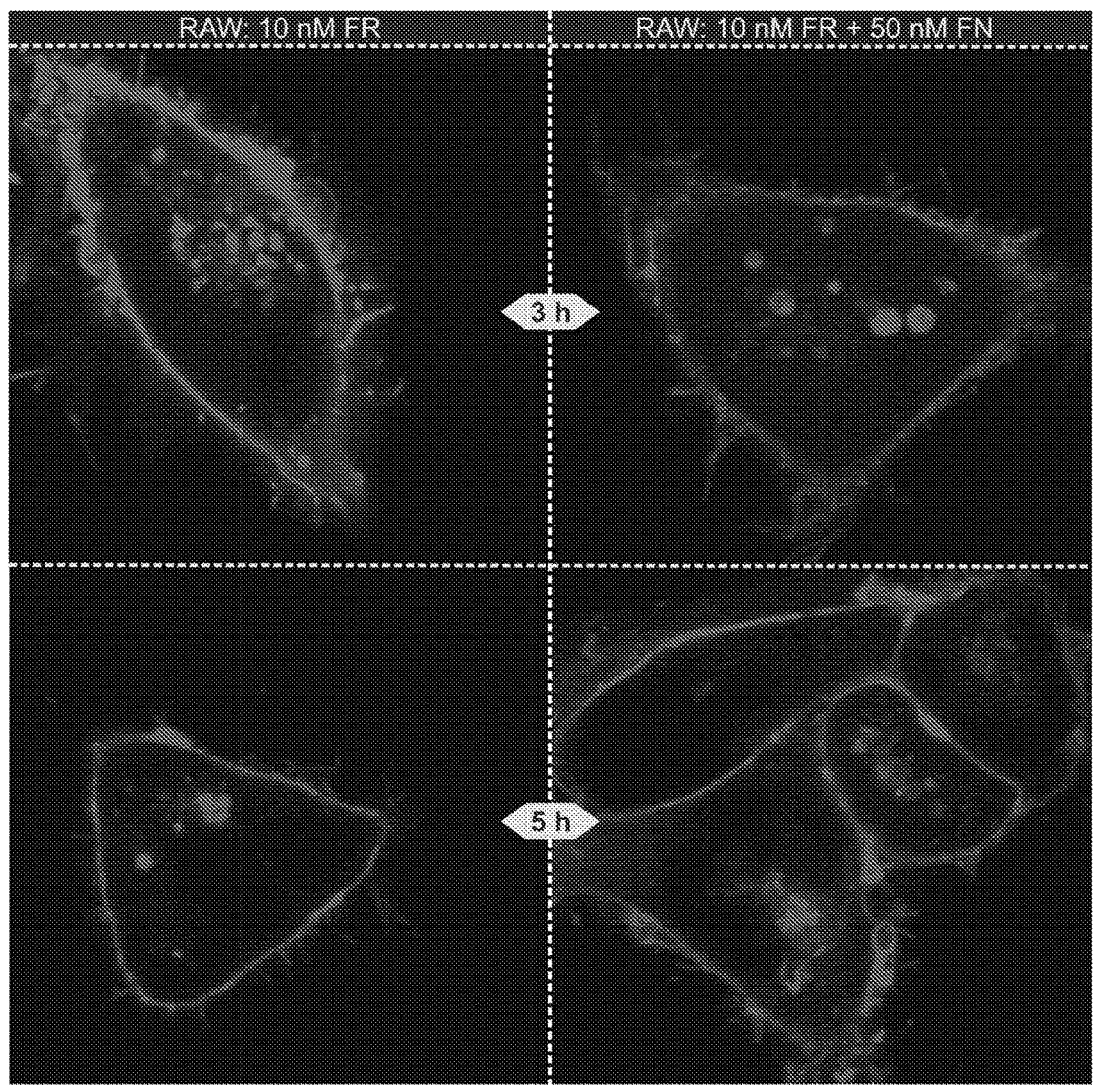
FIG. 10 shows escape of 10 nM FR (folate rhodamine compound) from endosomes in RAW cells as compared with RAW cells treated with both 10 nM FR and 50 nM FN (folate-nigericin conjugate).
Figure 11:
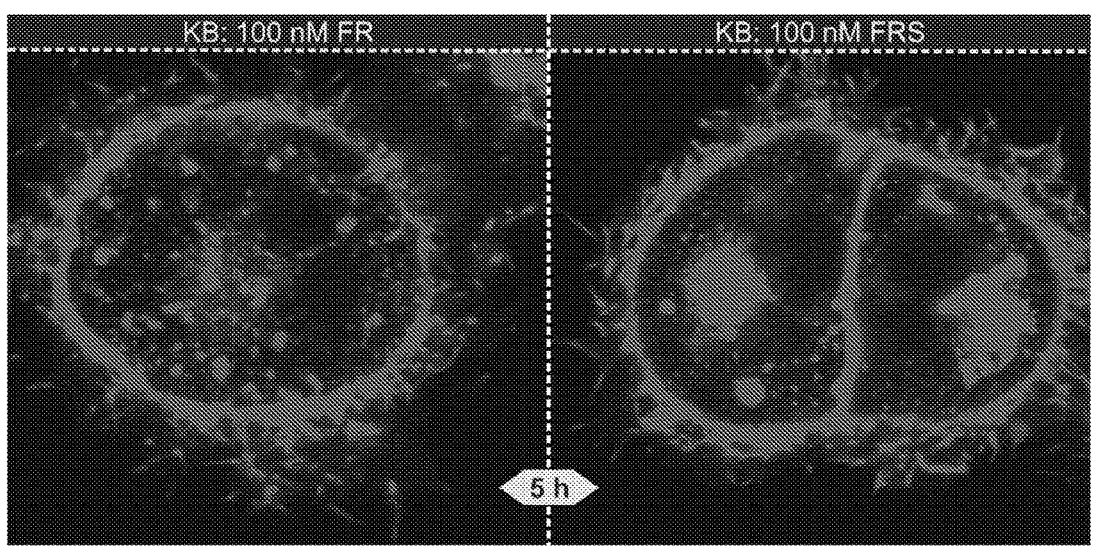
FIG. 11 shows KB cells treated with either 100 nM FR (folate rhodamine compound 2) or a 100 nM of single conjugate combining folate, salinomycin and rhodamine (folate-S-S-rhodamine-S-S-salinomycin conjugate).

Folate-Nigericin Conjugate. Another example of endosomal escape augmented by a folate-nigericin conjugate was investigated in FRβ-expressing RAW cells using 10 nM folate-rhodamine dye compound 2 (FR) with either 50 nM or 100 nM of folate-nigericin conjugate 1 (FN). By 2 h, all RAW cells, whether treated or untreated with folate-nigericin conjugate 1, exhibited significant accumulation of dye inside the endosomes, especially at the bilayer periphery (FIG. 9). The endosomes in cells treated with folate-nigericin conjugate 1 (100 nM) were somewhat larger than those inside untreated cells. At each time point shown in FIGS. 9-10, endosomal aggregation was more apparent in those cells treated with the nigericin conjugate.

miRNA-mediated suppression of *Renilla* luciferase. Attachment of a releasable nigericin ionophore to a folate-miRNA conjugate greatly increased the miRNA-mediated suppression of a target gene. The level of expression of the targeted gene (*Renilla* luciferase) was compared in a luciferase stably transfected cell line that was treated with a variety of formulations of microRNA. Formulations included untagged miR-34a, which was a double strand of miR34a; Fol-SS-Nig-NC, which was Folate-SS-Nigericin with scrambled RNA (Releasable); Fol-DB-Nig-NC, which was Folate-DBCO-Nigericin with scrambled RNA (non-releasable); Fol-DB-Nig-miR34a 3p, which was Folate-DBCO-Nigericin with single strand of passenger miR34a; Fol-DB-mir34a, which was Folate-DBCO-miR34a (non-releasable) without nigericin; Fol-SS-mir34a, which was Folate-SS-DBCO-miR34a (releasable) without nigericin; Fol-SS-Nig-mir34a, which was Folate-SS-nigericin-DBCO-miR34a (releasable) with nigericin; and Fol-DB-Nig-mir34a, which was Folate-DBCO-nigericin-miR34a (non-relaesable) with nigericin. SS refers to disulfide, and DBCO refers to dibenzocyclooctyne. *Renilla* relative light units normalized were measured at 24 hours post treatment (FIG. 12) and at 48 hours post treatment (FIG. 13).

Figure 12:
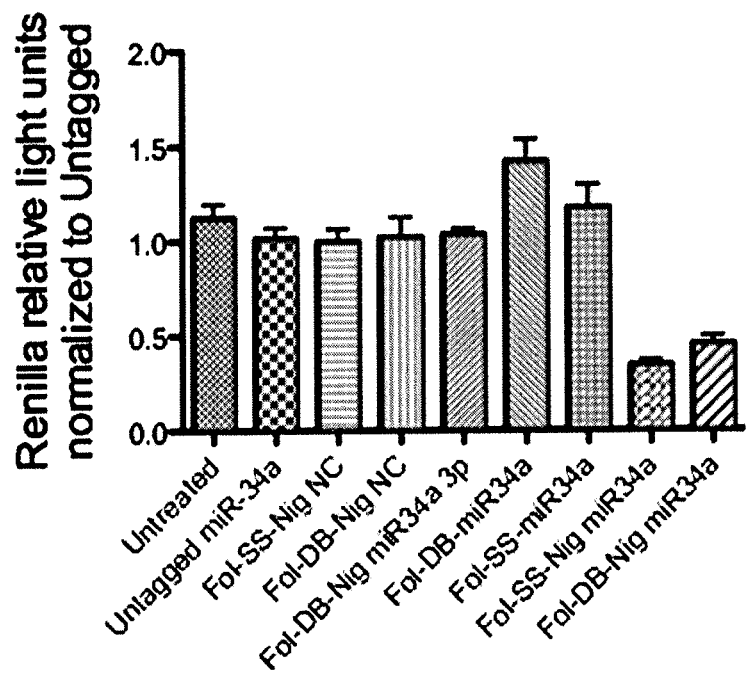
FIG. 12 shows *Renilla* relative light units normalized to untagged light units for cell lines treated with a variety of formulations of microRNA at 24 hours post treatment.
Figure 13:
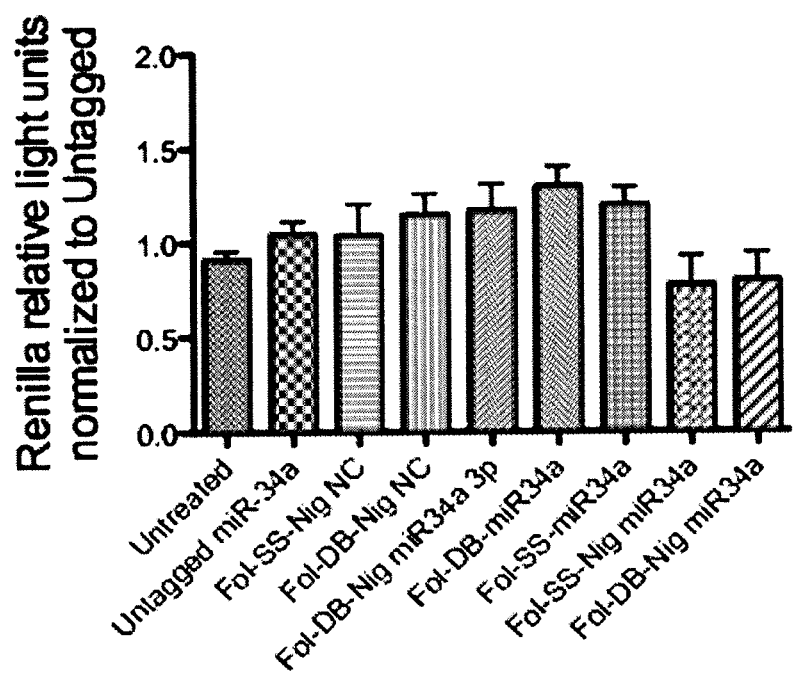
FIG. 13 shows *Renilla* relative light units normalized to untagged light units for cell lines treated with a variety of formulations of microRNA at 48 hours post treatment.

Referring to FIG. 12, the first bar on the left (untreated) shows the level of gene expression in the untreated cell line. The second bar from the left (untagged miR-34a) shows gene expression in the cell line treated with the nontargeted miRNA (no folate attached to deliver the miRNA into the cell). The third bar from the left (Fol-SS-Nig NC) has both folate for cell targeting/endocytosis and nigericin for endosomal escape, but the miRNA has a randomized sequence that does not cause gene suppression. The fourth bar from the left (Fol-DB-Nig NC) is the same as the third from the left but using a different linker chemistry. The fifth bar from the left (Fol-DB-Nig miRNA34a 3p) has active targeting and endosomal escape components but the miRNA chemistry is inactive. The sixth bar from the left (Fol-DB-miR34a) has folate for cell targeting and endocytosis, but no nigericin for endosomal escape. The seventh bar from the left (Fol-SS-miR34a) is the same as the sixth from the left but using a different linker chemistry. The eighth bar from the left (Fol-SS-Nig miR34a) has all active components; i.e. folate for cell targeting and endocytosis, nigericin for release of the miRNA from the endosomes, and the active sequence of miRNA. And the ninth bar from the left (Fol-DB-Nig miR34a) is the same as the eighth bar from the left except the linker chemistry is slightly different.

The data show that without an endosomal escape mechanism, the miRNA did not suppress its target gene, even if the miRNA is targeted to the cancer cell with folate and the cancer endocytoses the folate-miRNA conjugate into its endosomal compartment. That is, unless there was a mechanism to release the miRNA from its entrapping endosome, it was unable to reach its target in the cytosol of the cell.

This ability of nigericin (or salinomycin) to promote osmotic swelling and bursting of the endosome in which it is released can be exploited to release any biologic drug (e.g. protein, antibody, gene, siRNA, aptamer, peptide, mRNA, oligonucleotide, enzyme, hormone, carbohydrate, oligosaccharide, etc.) from an intracellular endosome into the cytoplasm where it can work.

What is claimed is:

1. A conjugate comprising:
   a ligand (B) that is a folate receptor binding ligand or a PSMA binding ligand;
   one or more linkers (L); and
   one or more ionophores (A) selected from the group consisting of nigericin and salinomycin which couples efflux of protons ($H^+$ ions) to influx of potassium ions ($K^+$ ions);
   wherein (L) comprises at least one releasable linker; (B) is covalently linked to (L); and each (A) is covalently linked to (L).

2. The conjugate of claim 1 further comprising a therapeutic agent, and/or an imaging agent wherein the therapeutic agent or the imaging agent is covalently linked to (L).

3. The conjugate of claim 1 further comprising a therapeutic agent covalently linked to (L), wherein the therapeutic agent comprises a low molecular weight drug, a polypeptide, a peptide, an oligonucleotide, a nucleotide, an siRNA, an iRNA, a microRNA, a ribozyme, an antisense oligonucleotide, a protein, a glycoprotein, an antibody, an antigen, a synthetic amino acid, an aptamer, an oligosaccharide, or a polysaccharide.

4. The conjugate of claim 3 wherein the therapeutic agent comprises a low molecular weight chemotherapeutic agent.

5. The conjugate of claim 3 wherein the therapeutic agent comprises a low molecular weight anti-inflammatory agent.

6. The conjugate of claim 1 further comprising a fluorescent dye covalently linked to (L).

7. The conjugate of claim 1 wherein (B) is a folate.

8. The conjugate of claim 1 wherein (B) is a PSMA binding ligand.

9. The conjugate of claim 1 wherein (A) is an inhibitor of the $Na^+/H^+$ exchanger.

10. The conjugate of claim 1 wherein (L) comprises a chain of about 7 to about 45 atoms.

11. The conjugate of claim 1 having a formula selected from the group consisting of

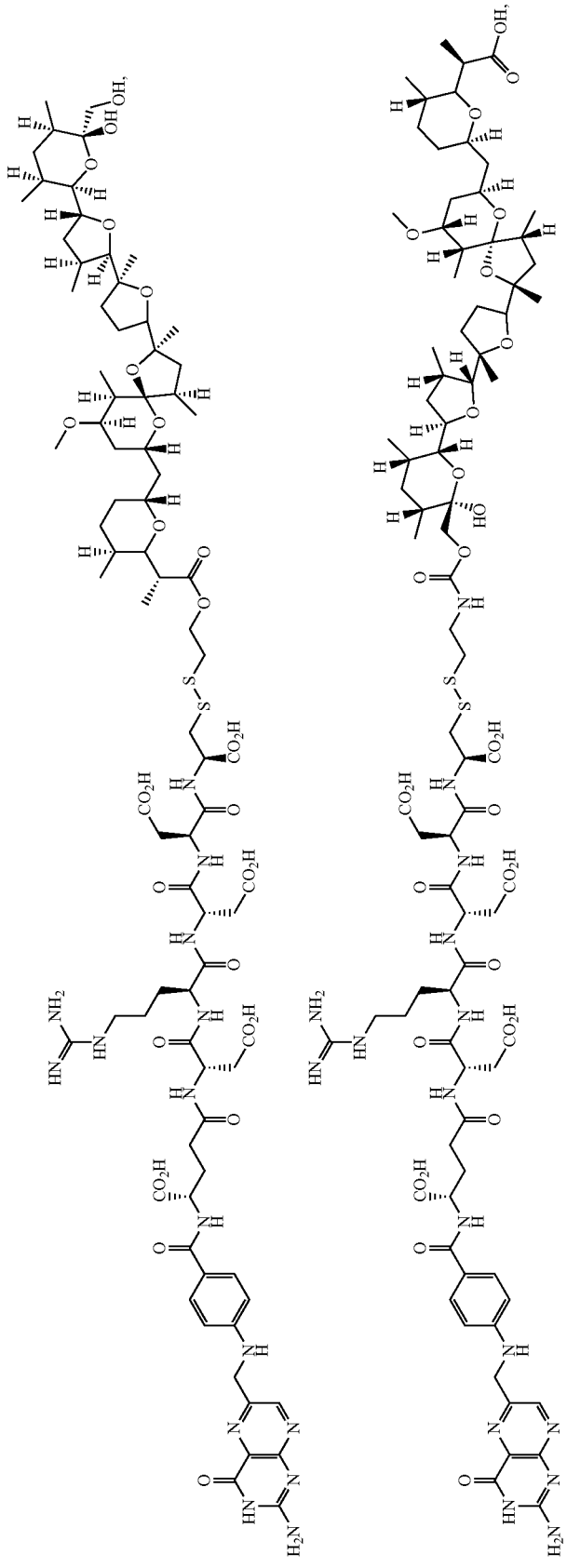

and
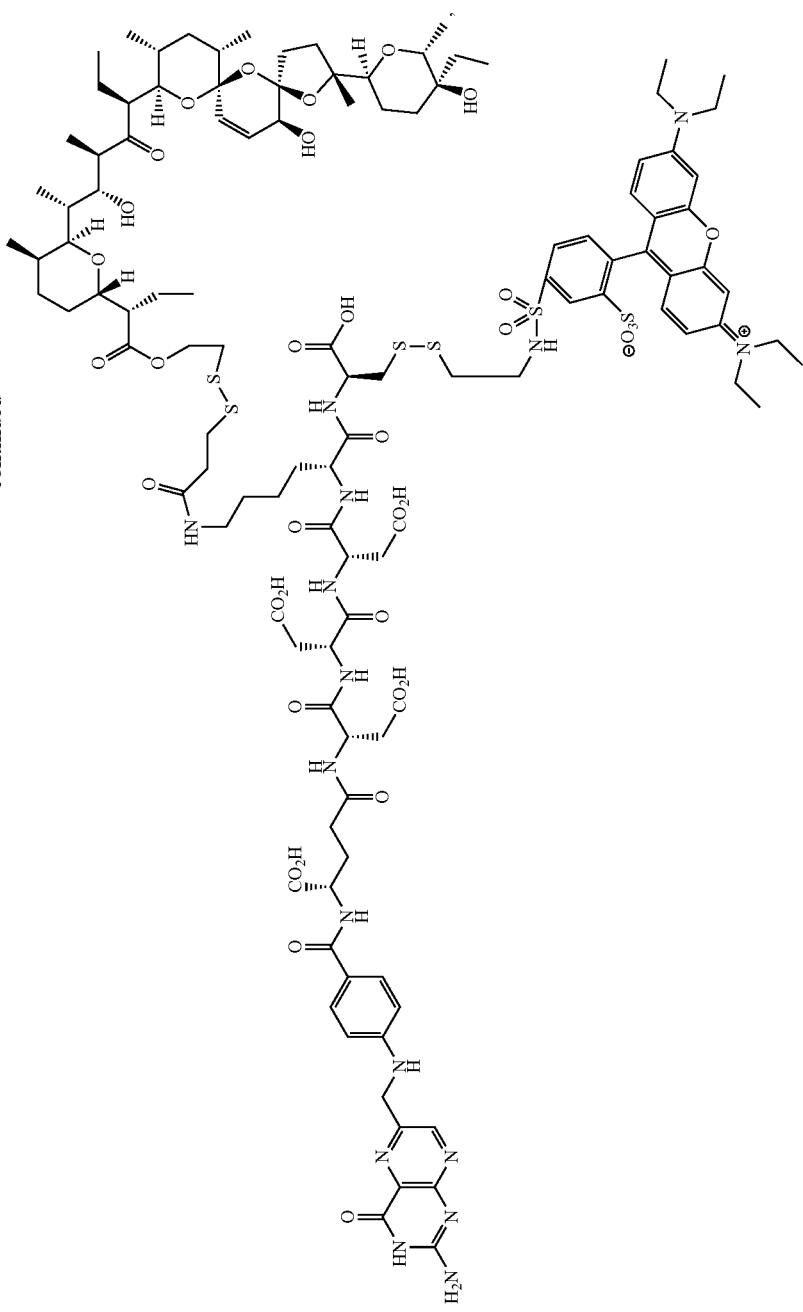

-continued
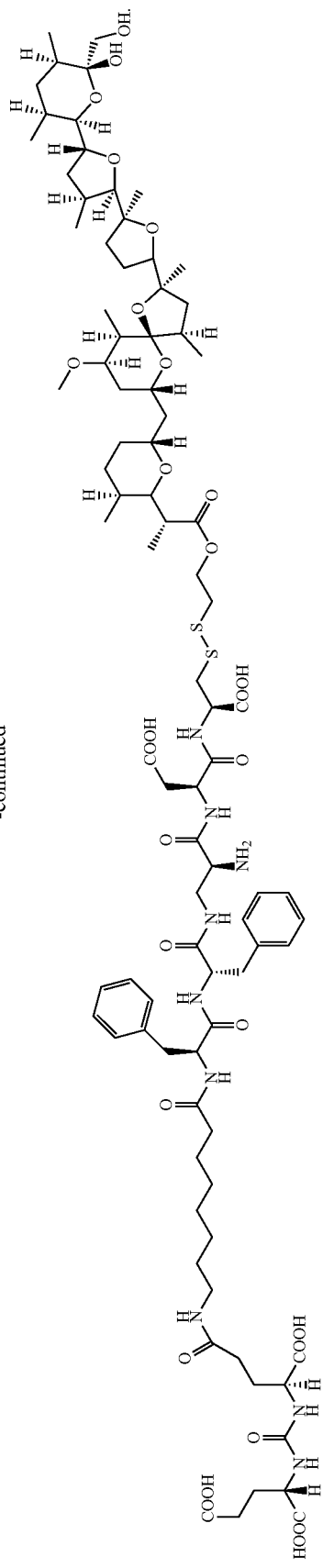

12. A pharmaceutical composition comprising the conjugate of claim 1 and at least one pharmaceutically acceptable carrier or excipient.

13. A pharmaceutical composition comprising the conjugate of claim 1 and at least one additional therapeutic agent.

14. A method of increasing the endosomal accumulation and escape of a therapeutic agent or an imaging agent, the method comprising the step of administering with the therapeutic agent or the imaging agent an effective amount of the conjugate of claim 1.

15. The method of claim 14 wherein the therapeutic agent or the imaging agent is targeted to a cancer.

16. The method of claim 15 wherein the cancer is selected from the group consisting of ovarian, lung, breast, endometrial, brain, kidney, prostate, and colon cancer.

17. The method of claim 14 wherein the therapeutic agent or the imaging agent is targeted to a site of inflammation.

18. The method of claim 17 wherein the inflammatory disease is selected from the group consisting of rheumatoid arthritis, osteoarthritis, atherosclerosis, diabetes, graft-versus-host disease, multiple sclerosis, osteomyelitis, psoriasis, Crohn's disease, Sjögren's syndrome, lupus erythematosus, and ulcerative colitis.

\* \* \* \* \*